United States Patent
Hashmonay

(10) Patent No.: US 7,501,629 B2
(45) Date of Patent: Mar. 10, 2009

(54) FENCELINE MONITORING OF AIR CONTAMINANTS

(75) Inventor: Ram A. Hashmonay, Chapel Hill, NC (US)

(73) Assignee: Arcadis G & M Inc., Durham, NC (US)

( * ) Notice: Subject to any disclaimer, the term of this patent is extended or adjusted under 35 U.S.C. 154(b) by 185 days.

(21) Appl. No.: 11/386,450

(22) Filed: Mar. 22, 2006

(65) Prior Publication Data
US 2007/0045542 A1 Mar. 1, 2007

Related U.S. Application Data

(60) Provisional application No. 60/664,085, filed on Mar. 22, 2005.

(51) Int. Cl.
*G01N 21/00* (2006.01)
(52) U.S. Cl. ................................. 250/339.08
(58) Field of Classification Search ............. 250/339.08
See application file for complete search history.

(56) References Cited

U.S. PATENT DOCUMENTS 6,542,242 B1 * 4/2003 Yost et al. .................. 356/450
6,776,523 B2 8/2004 Simunovic et al.
2006/0203248 A1 * 9/2006 Reichardt et al. ........... 356/437

OTHER PUBLICATIONS

Hashmonay et al., "Localizing Gaseous Fugitive Emission Sources by Combining Real-Time Optical Remote Sensing and Wind Data," J Air and Waste Management Assoc., vol. 49, pp. 1374-1379 (1999).
Thoma et al., "Open-Path Tunable Diode Laser Absorption Spectroscopy for Acquisition of Fugitive Emission Flux Data," J Air and Waste Management Assoc., 55, 658-668 (2005).
Xiao et al., "A Transportable, Remote Sending, Infrared Air-Monitoring System," Am. Ind. Hyg. Assoc. J., vol. 52, pp. 449-457 (1991).
Yost et al., "Estimating Maximum Concentrations for Open Path Monitoring Along a Fixed Beam Path," J Air and Waste Management Assoc., vol. 49, pp. 424-433 (1999).

* cited by examiner

*Primary Examiner*—David P Porta
*Assistant Examiner*—Marcus H Taningco
(74) *Attorney, Agent, or Firm*—Jenkins, Wilson, Taylor & Hunt, P.A.

(57) ABSTRACT

Methods, systems, and computer program products for the fenceline monitoring of air contaminants. More particularly, methods, systems, and computer program products for correlating temporal variations between simultaneous measurements of at least one point monitor and an optical remote sensing (ORS) monitor to estimate the peak concentration of one or more air contaminants along a line of measurement, e.g., a fenceline.

12 Claims, 7 Drawing Sheets

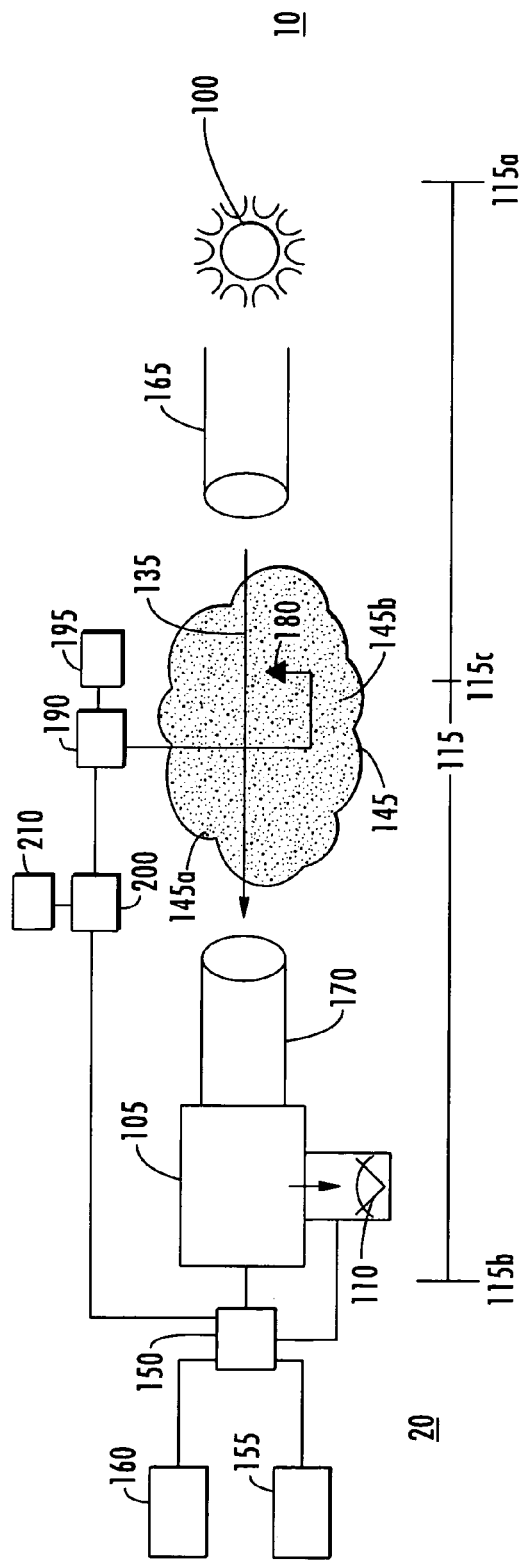
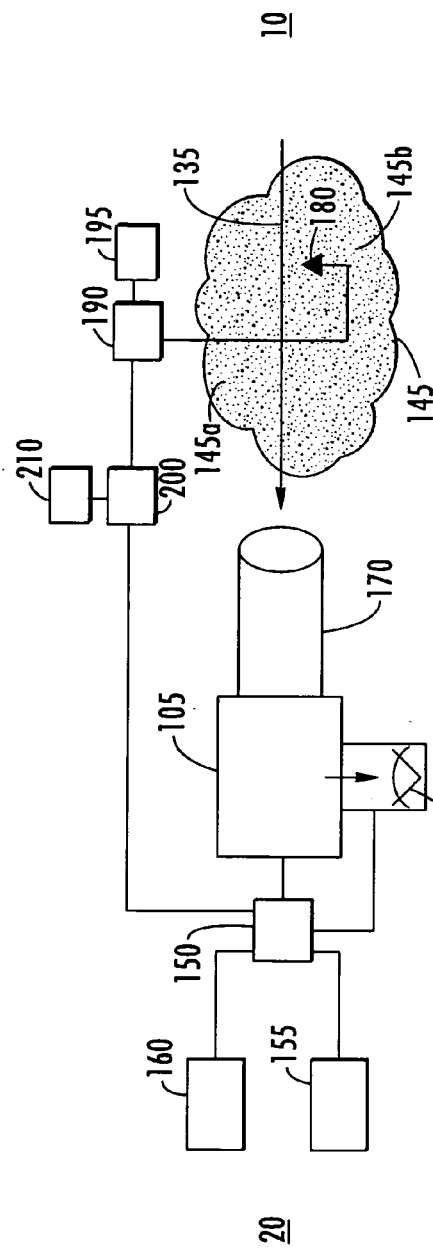
FIG. 3A
FIG. 3B

FENCELINE MONITORING OF AIR CONTAMINANTS

CROSS REFERENCE TO RELATED APPLICATIONS

This application is based on and claims priority to U.S. Provisional Patent Application Ser. No. 60/664,085, filed Mar. 22, 2005, which is incorporated herein by reference in its entirety.

TECHNICAL FIELD

The presently disclosed subject matter relates to methods, systems, and computer program products for the fenceline monitoring of air contaminants. More particularly, the presently disclosed subject matter relates to methods, systems, and computer program products for correlating temporal variations between simultaneous measurements of at least one point monitor and a monitor, such as an optical remote sensing (ORS) monitor, which is capable of measuring a path-averaged or path-integrated concentration along a monitoring path, to estimate the peak concentration of one or more air contaminants along a line of measurement, e.g., a fenceline.

ABBREVIATIONS

AEGL=acute exposure guideline level
CLS=classical-least-squares
CWA=chemical warfare agent
DMMS=depot area air monitoring system
FTIR=Fourier transform infrared
g=gram
IDLH=immediately dangerous to life and health
IR =infrared
K=degrees Kelvin
m=meter
MCT=mercury-cadmium-telluride
mg=milligram
NIR=near infrared
NRT=near real-time
OP=open path
OP-IR=open-path infrared
OP-FTIR=open-path Fourier transform infrared
ORS=optical remote sensing
OSHA=Occupational Safety and Health Administration
PM=particulate matter
ppb=parts per billion
ppb-m=parts per billion-meter
ppm=parts per million
ppm-m=parts per million-meter
TDL=tunable diode laser
TIC=toxic industrial chemical
µg=microgram
µm=micrometer

BACKGROUND

The fenceline monitoring of air contaminants is applicable to, but not limited to, the monitoring of toxic chemicals emitted from industrial facilities, the potential release of chemical warfare agents from chemical weapon stockpiles, and the monitoring of particulate matter (PM), such as dust. One approach to the fenceline monitoring of such air contaminants involves the installation of individual monitoring stations, i.e., point monitors, around the perimeter of the facility of interest at a predetermined distance from each other with the hope that the emission plumes will impact the point monitors. Another approach, which provides better coverage of the fenceline and increases the likelihood of capturing the emission plume, uses a monitor, such as an optical remote sensing (ORS) monitor, which is capable of measuring the path-integrated or path-averaged concentration of one or more target species along a monitoring path. These approaches, however, have limitations in determining the peak or maximum concentrations of such emissions along a line of measurement, such as a fenceline.

Primarily due to cost considerations, point monitors typically are sparsely positioned along the fenceline. In such a monitoring configuration, the point monitors randomly detect point concentrations that only rarely coincide with the peak or maximum concentration of the passing plume. Furthermore, plumes, or a substantial portion of a plume, can be totally ignored if the plume or a substantial portion of the plume passes between two point monitors.

On the other hand, ORS methods, or equivalent methods, capture all plumes that cross the beam path, i.e., a beam path along a fenceline, but only provide path-averaged or path-integrated concentrations. When assessing potential human exposure along a beam path, however, the path-averaged concentration is not always informative because concentrations along the path can vary substantially from the beam average. For example, the path-averaged concentration can underestimate the peak concentration by an order of magnitude for a plume width corresponding to one tenth of the beam's physical path-length.

Accordingly, point monitoring and ORS separately provide only partial solutions for complete fenceline protection and estimation of maximum concentrations. Yost et al., *J. Air & Waste Manage. Assoc.*, 49, 424-433 (1999), which is incorporated herein by reference in its entirety, have reported a method that uses a combination of several point monitors concurrently deployed with a single-path ORS monitor for estimating the maximum concentration along a line of measurement. The method described by Yost et al., however, requires several point monitors (at least three) along the line of measurement. This requirement makes this method complex and expensive. Another drawback to this method is that it overlooks an advantage of ORS instrumentation—high temporal resolution.

Accordingly, there is a need in the art for providing an estimate of the peak or maximum concentration of all plumes crossing the fenceline of a facility, not merely those plumes which by chance impact the point monitors.

SUMMARY

In some embodiments, the presently disclosed subject matter provides a method for estimating a maximum concentration of one or more target species along a line of measurement, the method comprising:
(a) providing a first monitor capable of producing a signal indicative of one of a path-integrated concentration and a path-averaged concentration of the one or more target species along a line of measurement;
(b) selecting a line of measurement comprising a first end point and a second end point;
(c) positioning the first monitor along the line of measurement at a monitoring path defined by the first end point and the second end point of the line of measurement;
(d) positioning at least one point monitor at one or more predetermined locations between the first end point and the second end point of the line of measurement, wherein the at least one point monitor is capable of producing a signal indicative of one or more concentrations of the one or more target species at the one or more predetermined locations;

(e) simultaneously measuring one of the path-integrated concentration and path-averaged concentration and the one or more concentrations of the one or more target species at the one or more predetermined locations; and (f) correlating a temporal variation between one of the path-integrated concentration and path-averaged concentration and the one or more concentrations of the one or more target species at the one or more predetermined locations to estimate a maximum concentration of the one or more target species along the line of measurement.

In some embodiments, the presently disclosed subject matter provides a system for estimating a maximum concentration of one or more target species along a line of measurement, the system comprising:

(a) a first monitor capable of producing a signal indicative of one of a path-integrated concentration and a path-averaged concentration of the one or more target species along the line of measurement;

(b) at least one point monitor adapted for positioning at one or more predetermined locations between the first end point and the second end point of the line of measurement, wherein the at least one point monitor is capable of producing a signal indicative of one or more concentrations of the one or more target species at the one or more predetermined locations;

(c) a memory in which a plurality of machine instructions are stored; and (d) at least one processor that is coupled to the at least one detector, the at least one point monitor, and the memory, wherein the processor is capable of executing the plurality of machine instructions stored in the memory, causing the processor to:

(i) simultaneously record the signal indicative of one of a path-integrated concentration and a path-averaged concentration of the one or more target species along the line of measurement and the signal indicative of one or more concentrations of the one or more target species at the one or more predetermined locations; and (ii) correlate a temporal variation between the signal indicative of one of a path-integrated concentration and a path-averaged concentration of the one or more target species along the line of measurement and the signal indicative of one or more concentrations of the one or more target species at the one or more predetermined locations to estimate a maximum concentration of the one or more target species along the line of measurement.

In some embodiments, the presently disclosed subject matter provides a computer program product comprising computer-executable instructions embodied in a computer-readable medium for performing steps comprising:

(a) inputting a signal indicative of one of a path-integrated concentration and a path-averaged concentration of one or more target species along a line of measurement;

(b) inputting a signal indicative of one or more concentrations of one or more target species at one or more predetermined locations along a line of measurement; and (c) correlating a temporal variation between the signal indicative of one of a path-integrated concentration and a path-averaged concentration of the one or more target species along the line of measurement and the signal indicative of one or more concentrations of the one or more target species at the one or more predetermined locations along the line of measurement to estimate a maximum concentration of the one or more target species along the line of measurement.

Thus, the presently disclosed subject matter provides methods, systems, and computer program products for correlating temporal variations between simultaneous measurements of at least one point monitor and a monitor, such as an optical remote sensing (ORS) monitor, which is capable of measuring the path-integrated or path-averaged concentration, to estimate the peak or maximum concentration of one or more air contaminants along a line of measurement, e.g., a fenceline. Air contaminants for which the presently disclosed subject matter is applicable include, but are not limited to, industrial toxic chemicals, chemical warfare agents, and particulate matter (PM). Indeed the presently disclosed subject matter is applicable to any air contaminant that exhibits one or more absorption bands or spectral features, such as a baseline offset, in the mid-infrared spectral region, e.g., from about 5000 cm$^{-1}$ to about 500-cm$^{-1}$, or can be measured by a tunable diode laser system operating in the near-infrared spectral region, e.g., in the 0.6- to 2.0-µm wavelength region, and in some embodiments, in the 1.4- to 1.8-µm wavelength region.

In some embodiments, the line of measurement comprises a monitoring path along the perimeter of a facility. In some embodiments, the facility is a facility having one or more potential air contaminants disposed therein. In some embodiments, the instrument is selected from the group consisting of an open-path Fourier transform infrared (OP-FTIR) monitor and a tunable diode laser (TDL) monitor. In some embodiments, the predetermined location of the at least one point monitor is about a midpoint between a first end point and a second end point of the line of measurement.

Accordingly, it is an object of the presently disclosed subject matter to provide novel methods, systems, and computer program products for monitoring the peak or maximum concentration of one or more air contaminants along a line of measurement, e.g., a fenceline. This and other objects are achieved in whole or in part by the presently disclosed subject matter.

An object of the presently disclosed subject matter having been stated hereinabove, other objects and aspects will become evident as the description proceeds when taken in connection with the accompanying Drawings and Examples as best described herein below.

BRIEF DESCRIPTION OF THE DRAWINGS

FIG. 2A is an active, modulated monostatic ORS system in which the active, modulated energy source and the detector are positioned at the same end of the monitoring path, and the transmitted optical beam and the returned optical beam travel along substantially an identical path.

FIG. 2B is an active, modulated monostatic ORS system in which the active, modulated energy source and the detector are positioned at the same end of the monitoring path, and wherein the transmitted optical beam is translated such that the returned optical beam traverses a path that is offset with respect to the path traversed by the transmitted optical beam.

FIG. 2C is an active, modulated bistatic ORS system in which the energy source and the detector are positioned at opposite ends of the monitoring path.

FIGS. 3A and 3B are schematic representations of ORS systems in which the energy source, either an active energy source or ambient background radiation, is not modulated before the optical beam is transmitted along the monitoring path.

FIG. 3A is an active bistatic ORS system in which the energy source and the detector are positioned at opposite ends of the monitoring path.

FIG. 3B is a passive ORS system in which the ambient background in the field of view of the receiving optics supplies the radiation, e.g., mid-infrared radiation, which interrogates the plume.

DETAILED DESCRIPTION

Figure 1:
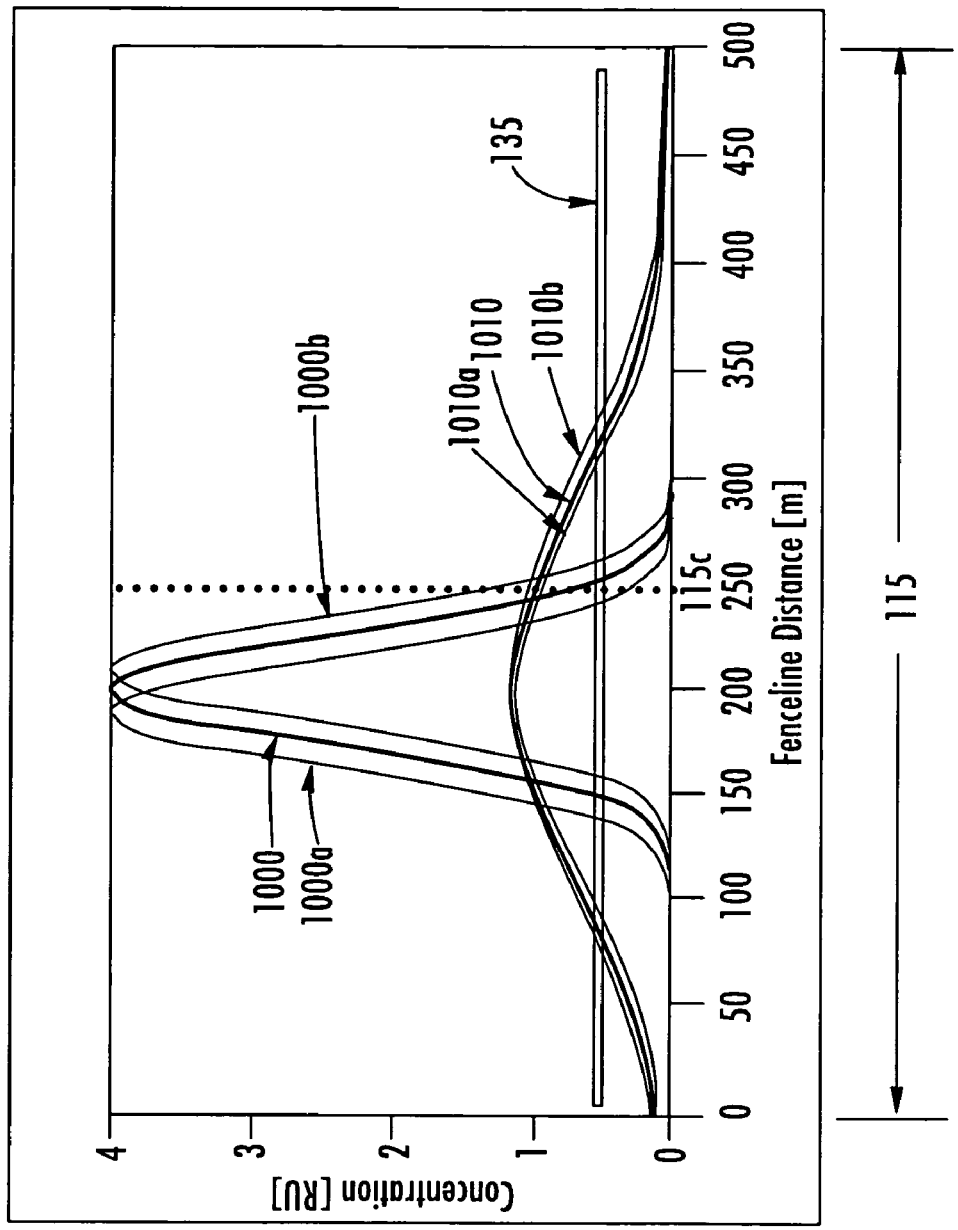
FIG. 1 is a diagram depicting an embodiment of the presently disclosed method for estimating the peak concentration of one or more target species along a line of measurement.

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

I. Definitions

As used herein, the terms "open-path monitoring" and "optical remote sensing" are used interchangeably and refer to monitoring over a location in space, i.e., a "monitoring path" or "a line of measurement," that is open to the atmosphere.

An "optical remote sensing monitor" refers to an optical system comprising an energy source, i.e., a radiation source, such as a mid-infrared source, a near-infrared source, or an ultraviolet source, capable of emitting energy along a path and at least one detector capable of detecting the energy emitted by the energy source, wherein the detector produces a signal indicative of the path-averaged or path-integrated concentration of the species of interest along the path. For an overview of optical remote sensing monitors and methods of use thereof, see ASTM E-1865-97, Standard Guide for Open-Path Fourier Transform Infrared (OP/FT-IR) Monitoring of Gases and Vapors in Air; ASTM E 1982-98, Standard Practice for Open-Path Fourier Transform Infrared (OP/FT-IR) Monitoring of Gases and Vapors in Air; U.S. Pat. No. 6,542,242 to Yost et al.; and E. D. Thoma, et al., Open-Path Tunable Diode Laser Absorption Spectroscopy for Acquisition of Fugitive Emission Flux Data, *J. Air & Waste Manage. Assoc.*, 55:658-668 (2005), each of which is incorporated herein by reference in its entirety.

Examples of an optical remote sensing (ORS) monitor suitable for use with the presently disclosed methods, systems, and computer program products include, but are not limited to, an open-path Fourier transform infrared (OP-FTIR) monitor and a tunable diode laser (TDL) monitor.

An "active" ORS system refers to an ORS system that comprises an energy source, such as an infrared source, a near-infrared source or an ultraviolet source, which supplies the optical beam to be transmitted along the monitoring path.

A "passive" ORS system refers to an ORS system that relies on energy emitted from a blackbody radiation source in the field of view of the receiving optics to supply the optical beam which interrogates, for example, a plume comprising one or more air contaminants. A passive ORS system also can be used to measure the emission spectra of air contaminants in a plume, when the temperature of the plume is greater than the temperature of the ambient background.

The term "optical beam" refers to the energy emitted by an ORS instrument. In most ORS instruments, the energy emitted by the source, e.g., a mid-infrared source, a near-infrared source, or an ultraviolet source, is collimated by reflecting optics before it is transmitted along the monitoring path.

A "bistatic system" refers to an optical system in which the radiation source, e.g., a mid-infrared source, a near-infrared source, or an ultraviolet source, is positioned some distance from a detector. In ORS systems, this term generally means that the energy source and the detector are at opposite ends of the monitoring path.

A "monostatic system" refers to an optical system in which the radiation source and the detector are positioned at the same end of the monitoring path. In monostatic ORS systems, the optical beam generally is returned to the detector by a reflecting element, such as a retroreflector.

A "retroreflector" refers to an optical device that returns radiation, e.g., an optical beam, in a direction substantially the same as the direction from which it came. Retroreflectors come in a variety of forms. A type of retroreflector typically used in ORS measurements comprises three mutually perpendicular surfaces with which to return the optical beam in a direction substantially the same as the direction from which it came. This type of retroreflector is referred to as a "cube-corner retroreflector."

The term "monitoring path" refers to the location in space over which the presence of a gas, vapor, aerosol, particle, or combinations thereof, is monitored.

The term "monitoring pathlength" refers to the distance over which the optical beam traverses through the monitoring path.

The terms "parts per million meters" and "parts per billion meters" refer to the units associated with the quantity "path-integrated concentration" and are possible units of choice for reporting data from ORS monitors. The units are abbreviated as "ppm-m" and "ppb-m," respectively, and are independent of the monitoring pathlength.

The term "path-integrated concentration" refers to the quantity measured by an ORS system along the monitoring path. The path-integrated concentration is expressed in units of concentration times length, for example ppm-m or ppb-m, and is independent of the monitoring pathlength.

The term "path-averaged concentration" refers to the result of dividing the path-integrated concentration by the pathlength. The path-averaged concentration gives the average value of the concentration along the path, and typically is expressed in units of parts per million (ppm), parts per billion (ppb), or micrograms per cubic meter (µg/m³).

A "plume" refers to the gaseous and/or aerosol effluents emitted from an emission source and the volume of space the gaseous and/or aerosol effluents occupy. For example, a plume can be emitted from a pollutant source, such as a smoke stack, a chemical manufacturing plant, a chemical weapon storage site, and/or a landfill.

The term "aerosol" refers to a gaseous suspension of fine solid or liquid particles.

The term "vapor" refers to the gaseous state of a substance that is a liquid or a solid under standard temperature and pressure.

The term "air contaminant" refers to a substance that is present in the atmosphere that is harmful, injurious, and/or unpleasant to a living thing. Representative air contaminants include, but are not limited to, odorous compounds, noxious compounds, and toxic compounds, such as toxic industrial chemicals, including priority pollutants, compounds listed under the 1990 Clean Air Act Amendment, and common noxious atmospheric gases; chemical warfare agents; and particulate matter, such as dust. Representative air contaminants that can be monitored by the presently disclosed method, in particular by the presently disclosed OP-FTIR methods, are provided herein below in Table 1. Representative air contaminants that can be monitored by the presently disclosed method, in embodiments wherein the ORS system comprises a tunable diode laser, are provided in Table 2. Representative chemical warfare agents that can be monitored by the presently disclosed method are provided herein below in Table 3.

The phrase "immediately dangerous to life and health" or "IDLH" is defined by the Occupational Safety and Health Administration (OSHA) as an atmospheric concentration of any toxic, corrosive, or asphyxiant substance that poses an immediate threat to life, causes irreversible or delayed adverse health effects, or interferes with an individual's ability to escape from danger. Thus, in some embodiments, air contaminants are IDLH compounds.

The phrase "acute exposure guideline level" or "AEGL" describes the dangers to humans resulting from short-term exposure to airborne chemicals.

The term "target species" refers to a compound, such as, but not limited to, an air contaminant as defined hereinabove, including odorous compounds, noxious compounds, and toxic compounds, such as toxic industrial chemicals and chemical warfare agents, and particulate matter, such as dust, for which instrumental parameters are selected and analysis methods are developed to detect, identify, and/or quantify the one or more target species in the atmosphere.

The terms "monitor" and "monitoring" refer to the act of detecting, identifying and/or quantifying one or more target species in the atmosphere.

The term "apparent absorbance spectrum" refers to a measurement of an absorbance spectrum, i.e., a plot of absorbance units on the y-axis versus frequency (or wavelength) on the x-axis, wherein the features of the spectrum are a combination of the absorption features of the one or more target species and the extinction of the optical beam due to scattering by particles and/or aerosols in the optical beam.

A "background spectrum" refers to a spectrum, e.g., a single-beam spectrum, that does not contain the spectral features of the species of interest, e.g., the one or more target species.

A "single-beam spectrum" refers to the radiant power measured by the instrument detector as a function of frequency (or wavelength). In Fourier transform infrared spectrometry, the single-beam spectrum is obtained after a fast Fourier transform of an interferogram.

A "synthetic background spectrum" refers to a background spectrum that is generated by choosing points along the envelope of a single-beam spectrum and fitting a series of short, straight lines or a polynomial function to the chosen data points to simulate the instrument response in the absence of absorbing gases or vapors.

A "point monitor" refers to a monitor that measures the concentration of one or more target species at a single point or location, such as a predetermined location, along a line of measurement. Exemplary point monitors include, but are not limited to, an extractive Fourier transform infrared (FTIR) spectrometer system, for example, an FTIR system comprising an extractive gas cell, a flame ionization detector (FID), a photoionization detector (PID), an organic vapor analyzer (OVA), and a near-real time (NRT) gas analyzer, a gas chromatograph/mass spectrometer, a particulate matter (PM) monitor, and the like.

The term "fenceline" refers to a property line, perimeter, or outer boundary of, including, but not limited to, an industrial facility, a chemical weapons stockpile, a large area pollution source, a military base or camp, or a civilian residential area. A "fenceline" can define the monitoring path for ORS studies.

II. System, Method and Computer Program Product for Correlating Temporal Variations Between Simultaneous Measurements of at Least One Point Monitor and a Monitor Capable of Measuring Path-Integrated or Path-Averaged Concentration of a Target Species Along a Monitoring Path The presently disclosed subject matter provides, in some embodiments, the utilization of fast, synchronized, and simultaneous measurements of at least one single point monitor and a monitor, such as an ORS monitor, which is capable of measuring the path-integrated or path-averaged concentration of a target species along a monitoring path. In some embodiments, correlating the temporal variations between the two monitors allows for the use of only one point monitor in a beam-path, e.g., one point monitor positioned at one or more predetermined locations along a beam-path, for example, a midpoint of the beam-path, for a reliable estimation of the peak concentration. This configuration makes the method cost-effective by increasing the required spacing between adjacent point monitors up to the maximum path length of, for example, an ORS instrument (for example, approximately 500 m for open-path Fourier transform (OP-FTIR) monitors and 1 km for tunable diode laser (TDL) monitors). In addition to being cost effective, the presently disclosed method addresses the two basic needs of fenceline monitoring: substantially complete capture of the plume and a reliable estimate of the maximum concentration. Further, one of ordinary skill in the art would recognize that once a reliable estimate of the maximum or peak concentration is obtained, one can solve for the plume width from the peak concentration and the total mass obtained from the path-integrated concentration (PIC). Thus, the presently disclosed subject matter also can be used to determine the plume width and plume extent.

The presently disclosed subject matter can increase the accuracy of the estimation of the peak or maximum concentration of the one or more air contaminants along a line of measurement and can decrease the likelihood of false positives as compared to approaches currently available in the art. Further, the presently disclosed subject matter also can be used to generate data in real time to provide a warning of potential hazardous exposure to the one or more air contaminants.

The presently disclosed subject matter can be used to monitor for the release of one or more air contaminants along a fenceline, e.g., the property line and/or an outer boundary, of a facility having one or more potential air contaminants disposed therein, such as a chemical plant or a chemical weapon stockpile, or to monitor along the fenceline of a permanent or semi-permanent facility that houses one or more human occupants, such as a civilian residential area, a military base, or a military camp.

Referring now to the drawings, where like reference numerals refer to like parts throughout, and referring particularly to FIG. 1, shown are two two plumes, plume 1000 and plume 1010. Plume 1000 and plume 1010 represent the same total mass, but have a different dimension. Optical beam 135, for example an optical beam from an optical remote sensor (not shown), passes through plume 1000 and plume 1010, thereby measuring a path-integrated concentration of one or more target species comprising plume 1000 and plume 1010. In this example, the path-integrated concentration of plume 1000 and plume 1010 as measured by optical beam 135 will be the same.

Referring to FIGS. 1 and FIGS. 2A-2C, at least one point monitor 180 is located, for example, at predetermined location 115c, e.g., a midpoint, of path 115. In this example, point monitor 180 will read a higher concentration for plume 1010 than for plume 1000, which, as depicted in FIG. 1, has a higher peak, or maximum, concentration. Although peak monitor 180 provides an accurate estimate of the peak concentration of plume 1010, i.e., a wide plume, point monitor 180 severely underestimates the peak concentration of plume 1000, which as depicted in FIG. 1 is narrower than plume 1010. Further, use of point monitor 180 alone cannot discriminate between plume 1000 and plume 1010.

Additionally, as plume 1000 moves relative to predetermined location 115c of point monitor 180, wherein the movement of plume 1000 is shown as plume 1000a and plume 1000b and the movement of plume 1010 is shown as plume 1010a and plume 1010b, the one or more concentrations measured by point monitor 180 will fluctuate. In contrast, the path-integrated concentration measured by optical beam 135 will remain the same.

Thus, the presently disclosed subject matter provides methods wherein a temporal variability in one or more concentrations of one or more target species measured by at least one point monitor as compared to a temporal variability of the path-integrated concentration of the one or more target species as measured, for example, by an ORS system, can be used to estimate the peak concentration of the one or more target species. One of ordinary skill in the art would recognize upon a review of the present disclosure that any combination of temporally resolved path integrated concentration data and concentration data from at least one point monitor is suitable for use with the presently disclosed methods.

Accordingly, the presently disclosed subject matter provides a system, method, and computer program product for correlating temporal variations between simultaneous measurements of at least one point monitor and a monitor, such as an optical remote sensing (ORS) monitor, which is capable of measuring a path-integrated or path-averaged concentration of one or more target species along a monitoring path.

II.A. System for Correlating Temporal Variations Between Simultaneous Measurements of at Least One Point Monitor and a Monitor Capable of Measuring a Path-Integrated or Path-Averaged Concentration In some embodiments, the presently disclosed subject matter provides a system for estimating a maximum concentration of one or more target species along a line of measurement. The presently disclosed system includes an instrument, such as an optical remote sensing (ORS) monitor, adapted for emitting energy along a path. Referring now to FIGS. 2A-2C and 3A-3B, representative ORS systems, including active, modulated ORS systems, active, unmodulated ORS systems, and passive ORS systems, suitable for use with the presently disclosed subject matter are disclosed. Although OP-FTIR monitors and TDL monitors are provided herein as representative ORS monitors, one of ordinary skill in the art would recognize that other ORS monitors would be applicable to the presently disclosed method.

II.A.1. Active, Modulated Optical Remote Sensing Systems

Active, modulated optical remote sensing systems can be configured in a monostatic monitoring mode or a bistatic monitoring mode. In the monostatic configuration, the energy source and the detector are positioned at the same end of the monitoring path. A reflecting element, such as a retroreflector, is positioned at the opposite end of the monitoring point to return the optical beam to the detector. In this configuration, the optical pathlength is twice as long as the monitoring pathlength.

II.A.1.a. Active, Modulated Monostatic ORS Systems

Figure 2:
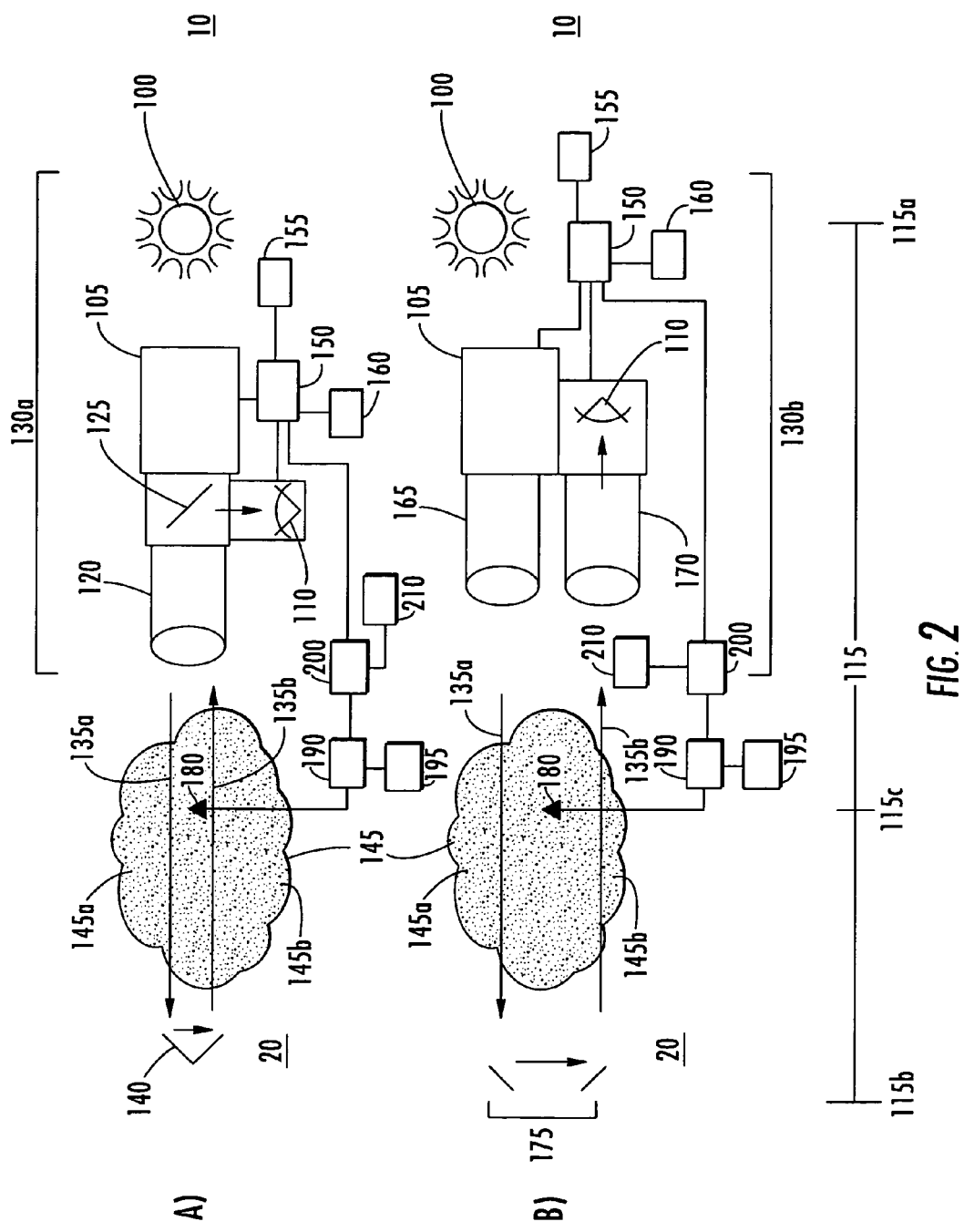
FIGS. 2A-2C are schematic representations of active, modulated ORS systems suitable for use with the presently disclosed subject matter.

Referring now to FIGS. 2A and 2B, representative systems 10 for estimating a maximum concentration of one or more target species along a line of measurement are provided. More particularly, FIGS. 2A and 2B provide schematic diagrams of two representative monostatic configurations of an ORS system 20 of the presently disclosed subject matter.

Referring now to FIG. 2A, energy source 100, wavelength separator 105, and detector 110 are all positioned at the same end, e.g., 115a, of monitoring path 115. In this configuration, transmitting/receiving optics 120 and beamsplitter 125 also are positioned at the same end, 115a, of monitoring path 115. Thus, spectrometer module 130a comprises energy source 100, wavelength separator 105, detector 110, transmitting/receiving optics 120, and beamsplitter 125. In some embodiments, transmitting/receiving optics 120 is selected from the group consisting of a Cassegrain telescope and a Newtonian telescope. Thus, ORS system 20 comprises an instrument adapted for emitting energy along a path, wherein energy from energy source 100 is emitted along path 115, which is defined by a first end point, e.g., 115a, and a second end point, e.g., 115b, of a line of measurement.

In some embodiments, energy source 100 comprises a broadband infrared energy source, such as a globar, i.e., a silicon carbide rod, and an incandescent wire comprising nichrome or rhodium sealed in a ceramic cylinder. In such embodiments, the energy emitted by energy source 100 is modulated by, for example, an interferometer, which can comprise wavelength separator 105 or a mechanical chopper (not shown).

In some embodiments, energy source 100 comprises a tunable diode laser, for example a tunable diode laser operating in the near-infrared spectral region.

Referring again to FIG. 2A, ORS system 20 comprises detector 110. Detector 110 detects the energy emitted by energy source 100 and produces a signal that is indicative of one of a path-integrated concentration and a path-averaged concentration of one or more target species, e.g., target species 145a and 145b, which comprise plume 145 along path 115. It is noted that target species 145a and 145b are provided for the purposes of illustration only. Upon review of the presently disclosed subject matter, one of ordinary skill in the art would recognize that the presently disclosed methods are not limited to two target species, but are applicable to measuring the concentrations of a plurality of target species.

In some embodiments, detector 110 comprises a thermal detector, such as a pyroelectric deuterated triglycine sulfate (DTGS) detector, which operates at room temperature. In some embodiments, detector 110 comprises a photoconducting detector, such as a mercury-cadmium-telluride (MCT) detector, which is cooled to liquid nitrogen temperatures.

Upon a review of the present disclosure, one of ordinary skill in the art would recognize that any energy source and any detector compatible with the energy source could be used in the presently described systems. The output power of the energy source should be stable. If the output power of the energy source is not stable, it should be controlled. Preferably, the power fluctuations of the energy source should be less than or on the order of the noise level of the system.

Also, the detection range of detector 110 should be matched to the spectral range of energy emitted by energy source 100. Accordingly, in some embodiments, the presently disclosed ORS systems comprise an energy source, detector, and other optical components, such as mirrors, beamsplitters, and the like, which are designed to operate in the mid-infrared spectral range (e.g., approximately a 2-μm to 20-μm (about 5000-cm$^{-1}$ to about 500-cm$^{-1}$) spectral range). In some embodiments, the ORS systems are designed to operate in the 4000-cm$^{-1}$ to 700-cm$^{-1}$ range. In some embodiments, the ORS systems are designed to operate in the approximately 1650-cm$^{-1}$ to 1250-cm$^{-1}$ range. In some embodiments, the ORS systems are designed to operate in the 1400-cm$^{-1}$ to 700-cm$^{-1}$ range. In some embodiments, the ORS systems are designed to operate in the 1100-cm$^{-1}$ to 900-cm$^{-1}$ range. In embodiments wherein the presently disclosed ORS systems comprise a tunable diode laser, the tunable diode laser can operate in the 0.6- to 2.0-μm wavelength region, and in some embodiments, in the 1.4- to 1.8-μm wavelength region.

Referring again to FIG. 2A, transmitting/receiving optics 120 are used to transmit and receive optical beams 135a and 135b along monitoring path 115. To transmit and receive optical beams 135a and 135b with the same telescopic optics, e.g., transmitting/receiving optics 120, beamsplitter 125 is positioned to divert part of returned optical beam 135b to detector 110. Thus, in this configuration, the optical beam, i.e., optical beams 135a and 135b, traverses beamsplitter 125 twice.

Referring once again to FIG. 2A, reflecting element 140 is positioned at an opposite end, e.g., 115b, of monitoring path 115. In this embodiment, reflecting element 140 comprises a single reflecting element, e.g., a cube-corner retroreflector array or a flat mirror, which returns optical beam 135 substantially along the same direction from which it was transmitted.

Continuing with FIG. 2A, energy, e.g., mid-infrared or near-infrared radiation, is emitted from energy source 100 and directed through wavelength separator 105, for example, an interferometer, where the energy is modulated at a predetermined frequency. In embodiments wherein the wavelength separator comprises an interferometer, the modulation frequency is wavelength dependent. The modulated energy exits wavelength separator 105, and in some embodiments, is collimated by transmitting/receiving optics 120 before it is transmitted along monitoring path 115, where it interrogates plume 145. Transmitted optical beam 135a is then redirected back toward opposite end 115b of monitoring path 115 by reflecting element 140. In some embodiments, reflecting element 140 comprises a cube-corner retroreflector array. In this configuration, reflecting element 140 returns transmitted optical beam 135a along substantially the same direction from which it came. Thus, the transmitted beam and returned beam travel along substantially the same path. Returned optical beam 135b is then collected by transmitting/receiving optics 120 and directed to detector 110 by beamsplitter 125. Detector 110 then records a signal that is indicative of the apparent absorbance spectrum of gases, vapors, aerosol, and particles, which is further indicative of one of a path-integrated concentration and a path-averaged concentration of one or more target species, e.g., target species 145a and 145b, comprising plume 145. Detector 110 is operatively coupled to processor 150. Processor 150 is bidirectionally coupled to memory 155, in which a plurality of machine instructions and/or data recorded by the ORS instrument are stored, and in some embodiments, to processor 200. In some embodiments, processor 200 is operationally coupled to memory 210, in which a plurality of machine instructions is stored. Processor 150 also can be operatively coupled to display/printer 160, which provides an image of the ORS data.

In some embodiments, ORS system 20 described in FIG. 2A comprises an open-path Fourier transform infrared system, in which the energy emitted from energy source 100 is modulated by wavelength separator 105, e.g., an interferometer. Thus, processor 150 can be instructed to accept only the modulated radiation from energy source 100 and to reject unmodulated ambient radiation. Accordingly, such a configuration allows the cancellation of background radiation that could introduce noise and error to the measurement due to atmospheric temperature scintillation effects.

Further, because detector 110 and wavelength separator 105 are at the same end of monitoring path 115, e.g., end 115a, the pathlength of monitoring path 115 is not limited by communication requirements between detector 110 and wavelength separator 105. For example, OP-FTIR monitors in a monostatic configuration can achieve a monitoring pathlength of about 500 m (optical pathlength of 1000 m).

Also, the monostatic configuration shown in FIG. 2A is adaptable to monitoring multiple paths in rapid succession. For example, a plurality of reflecting elements 140 can be positioned at a plurality of predetermined locations, e.g., a plurality of locations defined by a plurality of opposite ends 115b, to define a plurality of monitoring paths 115. In such a configuration, spectrometer module 130 comprising energy source 100, wavelength separator 105, detector 110, beamsplitter 125, and transmitting/receiving optics 120 can be mounted on a positioning device, such as a turntable (not shown), which allows spectrometer module 130a to be rotated in a horizontal plane, or a gimbal mechanism (not shown), which allows spectrometer module 130a to be maneuvered in three dimensions such that transmitting/receiving optics 120 direct optical beam 135 along a plurality of monitoring paths 115. Such positioning devices allow a single ORS spectrometer module, e.g., 130a, to be repositioned to scan a plurality of monitoring paths 115 in a horizontal plane, a vertical plane, and combinations thereof as desired. In such embodiments, the ORS system is referred to as a "scanning ORS system." See U.S. Pat. No. 6,542,242 to Yost et al., which is incorporated herein by reference in its entirety. Alternatively, instead of employing a mechanical positioning device, optical beam 135 can be optically steered to scan a plurality of monitoring paths 115. Accordingly, scanning ORS monitors can be used to provide surveillance over a large area.

Referring once again to FIG. 2A, system 10 for estimating a maximum concentration of one or more target species along a line of measurement further comprises at least one point monitor 180, which is adapted for positioning at predetermined location 115c between first end point 115a and second end point 115b. Point monitor 180 is capable of producing a signal indicative of one or more concentrations of one or more target species, e.g., target species 145a and 145b, comprising plume 145 at predetermined location 115c. Exemplary point monitors suitable for use with the presently disclosed subject matter include, but are not limited to, an extractive Fourier transform infrared (FTIR) spectrometer system, for example, an FTIR system comprising an extractive gas cell, a flame ionization detector (FID), a photoionization detector (PID), an organic vapor analyzer (OVA), and a near-real time (NRT) gas analyzer, a gas chromatograph/mass spectrometer, a particulate matter (PM) monitor, and the like. One of ordinary skill in the art would appreciate that any monitor that is capable of measuring one or more concentrations of a target species at a single point or location along a line of measurement can be used with the presently disclosed subject matter.

Referring once again to FIG. 2A, the signal from point monitor 180 is recorded by processor 190. In some embodiments, processor 190 is bidirectionally coupled to memory 195, in which a plurality of machine instructions and/or data recorded by the at least one point monitor are stored, and in some embodiments, to processor 200.

In some embodiments, processor 200 is operationally coupled to memory 210, in which a plurality of machine instructions is stored. Processor 200 is capable of executing the plurality of machine instructions stored in memory 210, causing processor 200 to (i) simultaneously record the signal, e.g., from detector 110, indicative of one of a path-integrated concentration and a path-averaged concentration of the one or more target species, e.g., target species 145a and 145b, comprising plume 145 along path 115 and the signal, e.g., from at least one point monitor 180, indicative of one or more concentrations of the one or more target species comprising plume 145 at the one or more predetermined locations, e.g., 115c; and (ii) correlate a temporal variation between the signal indicative of one of a path-integrated concentration and a path-averaged concentration of the one or more target species, e.g., target species 145a and 145b, comprising plume 145 along path 115 and the signal indicative of one or more concentrations of the one or more target species comprising plume 145 at predetermined location 115 to estimate a maximum concentration of the one or more target species along the line of measurement.

Referring now to FIG. 2B, and to ORS system 20 presented therein, and wherein like elements are identified by the same reference number as like elements in FIG. 2A, energy source 100, wavelength separator 105, transmitting optics 165, receiving optics 170, and detector 110 are each positioned at the same end, e.g., 115a, of monitoring path 115. Energy source 100, wavelength separator 105, transmitting optics 165, receiving optics 170, and detector 110 together comprise spectrometer module 130b. Reflecting element 175 is positioned at an opposite end, 115b, of monitoring path 115. In some embodiments, reflecting element 175 comprises an arrangement of mirrors, such as a single cube-corner retroreflector, that translates, e.g., shifts in a horizontal plane, transmitted optical beam 135a slightly so that is does not fold back on itself. In some embodiments, transmitting optics 165 and receiving optics 170 are each selected from the group consisting of a Cassegrain telescope and a Newtonian telescope.

Referring once again to FIG. 2B, receiving optics 170 are slightly removed from transmitting optics 165 so as to be in a position to receive returned optical beam 135b. In this configuration, detector 110 is disposed on an axis of returned optical beam 135b that is shifted in a horizontal plane relative to the axis of transmitted optical beam 135a.

In some embodiments, ORS system 20 described in FIG. 2B comprises an open-path Fourier transform infrared (OP-FTIR) system and, in some embodiments, ORS system 20 comprises a tunable diode laser (TDL) system. Energy (shown as a solid arrow) is emitted from energy source 100 and directed through wavelength separator 105, e.g., an interferometer, where the energy is modulated at a predetermined frequency. In embodiments wherein the wavelength separator comprises an interferometer, the modulation frequency is wavelength dependent. The modulated energy exits wavelength separator 105, and in some embodiments, is collimated by transmitting optics 165 before it is transmitted along monitoring path 115, where it interrogates plume 145. Transmitted optical beam 135a is then redirected back toward the opposite end, 115a, of monitoring path 115 by reflecting element 175. In some embodiments, reflecting element 175 comprises a single cube-corner retroreflector. As shown in FIG. 2B, reflecting element 175 translates returned optical beam 135b such that returned optical beam 135b and transmitted optical beam 135a are no longer traveling along identical paths. Returned optical beam 135b is then collected by receiving optics 170, then focused onto detector 110, which records a signal that is indicative of the apparent absorbance spectrum of gases, vapors, aerosol, and particles comprising plume 145.

Detector 110 is operatively coupled to processor 150. Processor 150 is bidirectionally coupled to memory 155, in which a plurality of machine instructions and/or data recorded by the ORS instrument are stored, and in some embodiments, to processor 200. In some embodiments, processor 200 is operationally coupled to memory 210, in which a plurality of machine instructions is stored. Processor 150 also can be operatively coupled to display/printer 160, which provides an image of the ORS data.

Referring once again to FIG. 2B, system 10 for estimating a maximum concentration of one or more target species along a line of measurement further comprises at least one point monitor 180, which is adapted for positioning at predetermined location 115c between first end point 115a and second end point 115b. Point monitor 180 is capable of producing a signal indicative of one or more concentrations of one or more target species, e.g., target species 145a and 145b, comprising plume 145 at predetermined location 115c. The signal from point monitor 180 is recorded by processor 190. In some embodiments, processor 190 is bidirectionally coupled to memory 195, in which a plurality of machine instructions and/or data recorded by the at least one point monitor are stored, and in some embodiments, to processor 200.

In some embodiments, processor 200 is operationally coupled to memory 210, in which a plurality of machine instructions is stored. Processor 200 is capable of executing the plurality of machine instructions stored in memory 210, causing processor 200 to (i) simultaneously record the signal, e.g., from detector 110, indicative of one of a path-integrated concentration and a path-averaged concentration of the one or more target species, e.g., target species 145a and 145b, comprising plume 145 along path 115 and the signal, e.g., from at least one point monitor 180, indicative of one or more concentrations of the one or more target species, e.g., target species 145a and 145b, comprising plume 145 at the one or more predetermined locations, e.g., 115c; and (ii) correlate a temporal variation between the signal indicative of one of a path-integrated concentration and a path-averaged concentration of the one or more target species, e.g., target species 145a and 145b, comprising plume 145 along path 115 and the signal indicative of one or more concentrations of the one or more target species comprising plume 145 at predetermined location 115 to estimate a maximum concentration of the one or more target species along the line of measurement.

Because initial alignment with this configuration can be difficult, this type of monostatic ORS system typically is used in permanent installations rather than as a transportable unit.

II.A.2. Active, Modulated Bistatic ORS Systems

In a bistatic configuration, the detector and the energy source are at opposite ends of the monitoring path. In this case, the optical pathlength is equal to the monitoring pathlength. In one bistatic configuration, the energy source, wavelength separator, e.g., an interferometer, and transmitting optics are positioned at one end of the monitoring path and the receiving optics and detector are positioned at the opposite end of the monitoring path.

Figure 2C:
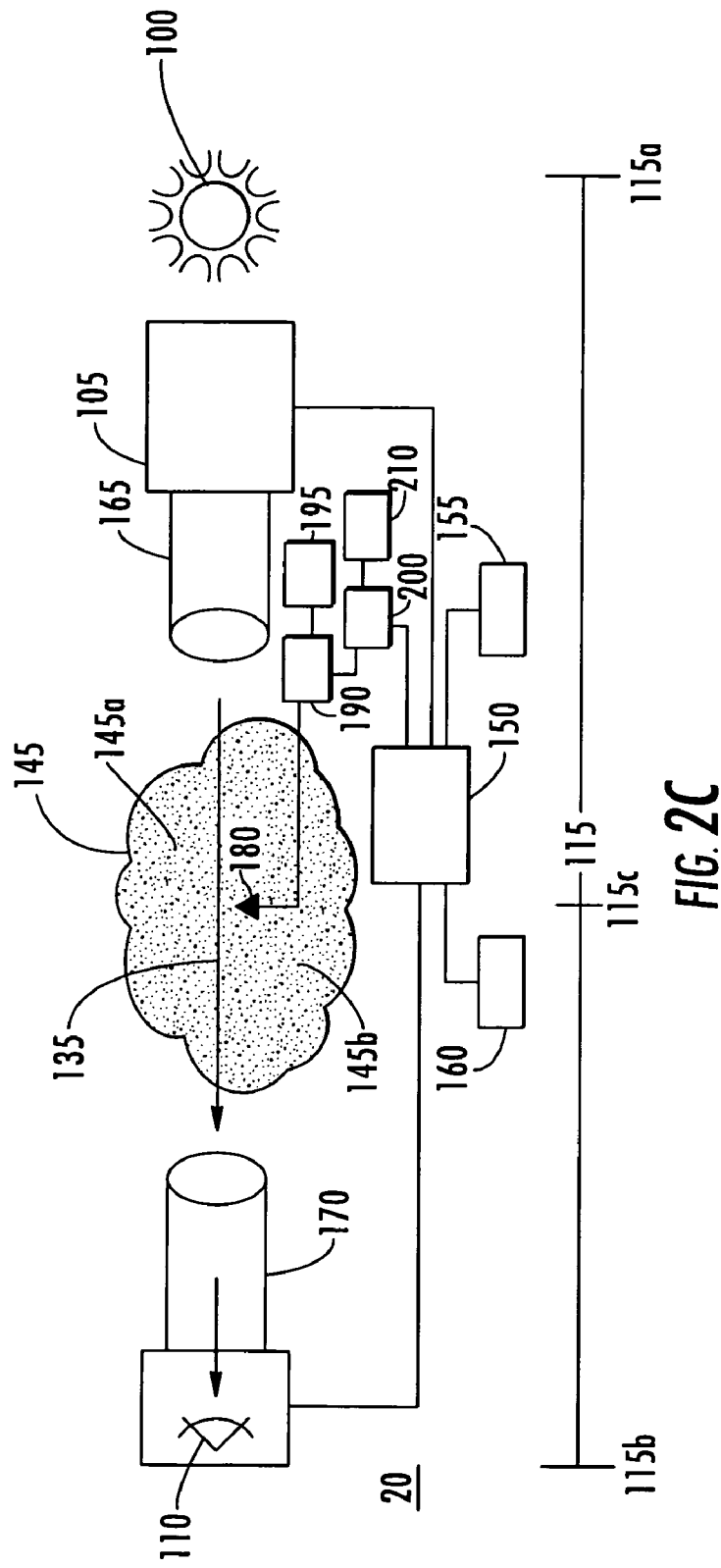

Referring now to FIG. 2C, a schematic diagram of an active, modulated bistatic ORS system 20 is presented, and like elements are identified by the same reference number as like elements in FIGS. 2A and 2B. Energy source 100, wavelength separator 105, and transmitting optics 165 are positioned at one end, 115a, of monitoring path 115 and receiving optics 170 and detector 110 are positioned at an opposite end, 115b, of monitoring path 115. Receiving optics 170 can comprise an optical telescope or other optical device that defines the field of view of the instrument.

Detector 110 is operatively coupled to processor 150. Processor 150 is bidirectionally coupled to memory 155, in which a plurality of machine instructions and/or data recorded by the ORS instrument are stored, and in some embodiments, to processor 200. In some embodiments, processor 200 is operationally coupled to memory 210, in which a plurality of machine instructions is stored. Processor 150 also can be operatively coupled to display/printer 160, which provides an image of the ORS data.

Referring once again to FIG. 2C, energy, e.g., mid-infrared or near-infrared radiation, is emitted from energy source 100 and directed through wavelength separator 105, e.g., an interferometer, where the energy is modulated at a predetermined frequency. In embodiments wherein the wavelength separator comprises an interferometer, the modulation frequency is wavelength dependent. The modulated energy exits wavelength separator 105, and in some embodiments, is collimated by transmitting optics 165 before it is transmitted along monitoring path 115, where it interrogates plume 145. Plume 145 can comprise a mixture of air contaminants, e.g., target species 145a and 145b, wherein the air contaminants can be in a gas phase, vapor phase, aerosol phase, adsorbed on airborne particulate matter, and combinations thereof, airborne particulate matter, and atmospheric gases. Optical beam 135 is then collected by receiving optics 170, then focused on detector 110, which records a signal that is indicative of the apparent absorbance spectrum of gases, vapors, aerosols, and particles comprising plume 145.

Referring once again to FIG. 2C, system 10 for estimating a maximum concentration of one or more target species along a line of measurement further comprises at least one point monitor 180, which is adapted for positioning at one or more predetermined locations, e.g., 115c, between first end point 115a and second end point 115b. Point monitor 180 is capable of producing a signal indicative of one or more concentrations of one or more target species, e.g., target species 145a and 145b, comprising plume 145 at predetermined location 115c. The signal from point monitor 180 is recorded by processor 190. In some embodiments, processor 190 is bidirectionally coupled to memory 195, in which a plurality of machine instructions and/or data recorded by the at least one point monitor are stored, and in some embodiments, to processor 200.

In some embodiments, processor 200 is operationally coupled to memory 210, in which a plurality of machine instructions is stored. Processor 200 is capable of executing the plurality of machine instructions stored in memory 210, causing processor 200 to (i) simultaneously record the signal, e.g., from detector 110, indicative of one of a path-integrated concentration and a path-averaged concentration of the one or more target species, e.g., target species 145a and 145b, comprising plume 145 along path 115 and the signal, e.g., from at least one point monitor 180, indicative of one or more concentrations of the one or more target species comprising plume 145 at the one or more predetermined locations, e.g., 115c; and (ii) correlate a temporal variation between the signal indicative of one of a path-integrated concentration and a path-averaged concentration of the one or more target species, e.g., target species 145a and 145b, comprising plume 145 along path 115 and the signal indicative of one or more concentrations of the one or more target species comprising plume 145 at predetermined location 115 to estimate a maximum concentration of the one or more target species along the line of measurement.

An advantage of the bistatic configuration shown in FIG. 2C is that optical beam 135 is modulated before it is transmitted along monitoring path 115. Processor 150 can be instructed to accept only the modulated radiation from the energy source and to reject unmodulated extraneous radiation, such as ambient or background radiation. Accordingly, such a configuration allows the cancellation of ambient or background radiation that could introduce noise and error to the measurement due to atmospheric temperature scintillation effects.

The maximum distance that wavelength separator 105 and detector 110 can be separated should be established with care, however, because communication between detector 110 and wavelength separator 105, e.g., an interferometer, is required for timing purposes during the acquisition of the spectrum. For example, a bistatic OP-FTIR system with this configuration developed for monitoring workplace environments had a maximum monitoring pathlength of about 40 m. See Xiao, H. K., et al., *Am. Ind. Hyg. Assoc. J.*, 52, 449 (1991).

II.A.3. Unmodulated Optical Remote Sensing Systems

Unmodulated optical remote sensing systems can acquire spectral data in an active mode or a passive mode. FIGS. 3A and 3B show representative configurations of unmodulated ORS systems.

II.A.3.a. Active, Unmodulated Bistatic ORS Systems

Referring now to FIG. 3A, another embodiment of ORS system 20 is presented, and like elements are identified by the same reference number as like elements in FIGS. 2A-2C. Energy source 100 and transmitting optics 165 are positioned at one end, e.g., 115a, of monitoring path 115 and receiving optics 170, wavelength separator 105, and detector 110 are positioned at the opposite end, e.g., 115b, of monitoring path 115. In this configuration, transmitting optics 165 typically comprise a paraboloid-shaped mirror, or other suitable collimating device, which collimates optical beam 135 before it is transmitted along monitoring path 115.

Referring once again to FIG. 3A, energy, e.g., mid-infrared or near-infrared radiation, is emitted from energy source 100 and is collimated by transmitting optics 170 before it is transmitted along monitoring path 115, where it interrogates plume 145. Optical beam 135 is then collected by receiving optics 170, directed through wavelength separator 105, and then focused on detector 110, which records a signal that is indicative of the apparent absorbance spectrum of gases, vapors, aerosol, and particles comprising plume 145.

Detector 110 is operatively coupled to processor 150. Processor 150 is bidirectionally coupled to memory 155, in which a plurality of machine instructions and/or data recorded by the ORS instrument are stored, and in some embodiments, to processor 200. In some embodiments, processor 200 is operationally coupled to memory 210, in which a plurality of machine instructions are stored. Processor 150 also can be operatively coupled to display/printer 160, which provides an image of the ORS data.

A consideration to the bistatic configuration shown in FIG. 3A is that the energy from energy source 100 is not modulated before it is transmitted along monitoring path 115. Therefore, energy emitted by energy source 100 and energy from the ambient background in the field of view of receiving optics 170 can be difficult to distinguish by electronic processing.

Another consideration to bistatic systems in general is that if multiple paths are to be monitored in rapid succession, e.g., by monitoring along different paths near different fencelines of an industrial facility, multiple sources or multiple detectors, or a combination of multiple sources and multiple detectors are required. This requirement can result in additional expense and complexity to the monitoring scheme.

Referring once again to FIG. 3A, system 10 for estimating a maximum concentration of one or more target species along a line of measurement further comprises at least one point monitor 180, which is adapted for positioning at one or more predetermined locations, e.g., 115c, between first end point 115a and second end point 115b. Point monitor 180 is capable of producing a signal indicative of one or more concentrations of one or more target species, e.g., target species 145a and 145b, comprising plume 145 at predetermined location 115c. The signal from point monitor 180 is recorded by processor 190. In some embodiments, processor 190 is bidirectionally coupled to memory 195, in which a plurality of machine instructions and/or data recorded by the at least one point monitor are stored, and in some embodiments, to processor 200.

In some embodiments, processor 200 is operationally coupled to memory 210, in which a plurality of machine instructions are stored. Processor 200 is capable of executing the plurality of machine instructions stored in memory 210, causing processor 200 to (i) simultaneously record the signal, e.g., from detector 110, indicative of one of a path-integrated concentration and a path-averaged concentration of the one or more target species, e.g., target species 145a and 145b, comprising plume 145 along path 115 and the signal, e.g., from at least one point monitor 180, indicative of one or more concentrations of the one or more target species comprising plume 145 at the one or more predetermined locations, e.g., 115c; and (ii) correlate a temporal variation between the signal indicative of one of a path-integrated concentration and a path-averaged concentration of the one or more target species, e.g., target species 145a and 145b, comprising plume 145 along path 115 and the signal indicative of one or more concentrations of the one or more target species comprising plume 145 at predetermined location 115 to estimate a maximum concentration of the one or more target species along the line of measurement.

II.A.4. Passive Optical Remote Sensing Systems

In contrast to the active ORS systems described hereinabove, a passive ORS system comprises a configuration that is similar to the bistatic configuration shown in FIG. 3A, except that the passive ORS system relies on ambient background radiation, which is emitted from natural surfaces that are only a few degrees different in temperature from the absorbing or emitting medium as the energy source.

Referring now to FIG. 3B, wherein like elements are identified by the same reference number as like elements in FIGS. 2A-2C and 3A, passive OR-IR system 20 comprises only the following optical components: receiving optics 170, wavelength separator 105, and detector 110. If the temperature of plume 145 is higher than the temperature of the ambient background in the field of view of receiving optics 170, the species comprising plume 145 will exhibit emission lines. If the temperature of the ambient background in the field of view of receiving optics 170 is higher than that of plume 145, the species comprising plume 145 will attenuate the radiation emitted by the ambient background and thus produce absorption lines.

In any event, after the ambient radiation interrogates plume 145, the radiation is detected by detector 110. Detector 110 is operatively coupled to processor 150. Processor 150 is bidirectionally coupled to memory 155, in which a plurality of machine instructions and/or data recorded by the ORS instrument are stored, and in some embodiments, to processor 200. In some embodiments, processor 200 is operationally coupled to memory 210, in which a plurality of machine instructions are stored. Processor 150 also can be operatively coupled to display/printer 160, which provides an image of the ORS data.

Referring once again to FIG. 3B, system 10 for estimating a maximum concentration of one or more target species along a line of measurement further comprises at least one point monitor 180, which is adapted for positioning at one or more predetermined locations, e.g., 115c, between first end point 115a and second end point 115b. Point monitor 180 is capable of producing a signal indicative of one or more concentrations of one or more target species, e.g., target species 145a and 145b, comprising plume 145 at predetermined location 115c. The signal from point monitor 180 is recorded by processor 190. In some embodiments, processor 190 is bidirectionally coupled to memory 195, in which a plurality of machine instructions and/or data recorded by the at least one point monitor are stored, and in some embodiments, to processor 200.

In some embodiments, processor 200 is operationally coupled to memory 210, in which a plurality of machine instructions are stored. Processor 200 is capable of executing the plurality of machine instructions stored in memory 210, causing processor 200 to (i) simultaneously record the signal, e.g., from detector 110, indicative of one of a path-integrated concentration and a path-averaged concentration of the one or more target species, e.g., target species 145a and 145b, comprising plume 145 along path 115 and the signal, e.g., from at least one point monitor 180, indicative of one or more concentrations of the one or more target species comprising plume 145 at the one or more predetermined locations, e.g., 115c; and (ii) correlate a temporal variation between the signal indicative of one of a path-integrated concentration and a path-averaged concentration of the one or more target species, e.g., target species 145a and 145b, comprising plume 145 along path 115 and the signal indicative of one or more concentrations of the one or more target species comprising plume 145 at predetermined location 115 to estimate a maximum concentration of the one or more target species along the line of measurement.

Because it can be difficult to distinguish between spectral features that are due to target species in the plume and spectral features that are due to fluctuations in the ambient background radiation, passive ORS systems are of limited utility for detecting, identifying, and quantifying low vapor pressure air contaminants in the atmosphere. Further, the high source temperature of an active ORS system can provide more than an 80-fold increase in the infrared radiant flux emitted per unit area in the 7-14-μm spectral fingerprint region compared to passive ORS systems. As a result, active ORS monitors can detect chemical warfare agents, such as, but not limited to GA, GB, GD, HD and Lewisite in the range of 1 to 10 μg/m$^3$ or below. These detection limits are orders of magnitude lower than those obtainable by passive ORS systems.

II.B. Method for Correlating Temporal Variations Between Simultaneous Measurements of at Least One Point Monitor and Monitor Capable of Measuring a Path-Integrated or Path-Averaged Concentration of One or More Target Species Along a Monitoring Path The presently disclosed subject matter provides a method for correlating temporal variations between simultaneous measurements of at least one point monitor and a monitor, such as an ORS monitor, capable of measuring a path-integrated or path-averaged concentration of one or more target species along a monitoring path, to estimate the peak concentration of one or more air contaminants along a line of measurement, e.g., a fenceline.

In some embodiments, the method for estimating a maximum concentration of one or more target species along a line of measurement includes providing an instrument adapted for emitting energy along a path. Any of the active ORS systems 20 shown in FIGS. 2A-2C, in which energy source 100 is modulated, are suitable for the presently disclosed methods. In some embodiments, the ORS system comprises an active, monostatic ORS system 20 as shown in FIG. 2A. One of ordinary skill in the art would recognize that the presently disclosed subject matter, however, is not limited to embodiments shown in FIGS. 2A-2C.

Referring once again to FIGS. 2A-2C, to monitor for air contaminants in the atmosphere using ORS system 20, a line of measurement, e.g., monitoring path 115, which is defined by a first end point, e.g., 115a, and a second end point, e.g., 115b, is first selected. Monitoring path 115 can be selected to run parallel, for example, to the fenceline of an industrial facility or a chemical weapons stockpile, along which air contaminants emitted from the industrial facility or chemical weapons stockpile are to be measured. In such embodiments, plume 145 comprising the one or more air contaminants, e.g., target species 145a and 145b, can pass across monitoring path 115 through a variety of mechanisms, including diffusion in the air, dispersion by prevailing wind currents, and the like.

Monitoring path 115 also can be positioned near the perimeter of, for example, a civilian residential area or a military base or camp, along which the potential release of air contaminants is monitored to provide an early warning to the civilians or military personnel housed therein. Monitoring path 115 also can be positioned downwind, for example, from a potential source of air contaminants to monitor for air contaminants comprising a plume resulting from dispersion of a plume of air contaminants released from the facility. Guidelines for selecting a monitoring path are provided in ASTM E 1865-97 Standard Guide for Open-Path Fourier Transform Infrared (OP/FT-IR) Monitoring of Gases and Vapors in Air and ASTM E 1982-98, Standard Practice for Open-Path Fourier Transform Infrared (OP/FT-IR) Monitoring of Gases and Vapors in Air, both of which are incorporated herein by reference in their entirety.

Once monitoring path 115 is selected, spectrometer module 130a, as shown in FIG. 2A, is positioned along a line of measurement, such that the position of spectrometer module 130a defines one end, e.g., 115a, of monitoring path 115. Reflecting element 140, e.g., a cube-corner retroreflector array, also is positioned along the line of measurement, at a predetermined distance from spectrometer module 130a, such that the position of reflecting element 140 defines an end, e.g. 115b, opposite that of end 115a of monitoring path 115. Ends 115a and 115b of monitoring path 115 should be selected so that they capture the expected plume, e.g., plume 145, of air contaminants, e.g., target species 145a and 145b.

Once monitoring path 115 is selected, at least one point monitor 180 is positioned at one or predetermined locations, e.g., 115c, along monitoring path 115. In some embodiments, predetermined location 115c is a midpoint between ends 115a and 115b of monitoring path 115.

Once ORS system 20 is set-up along the line of measurement, e.g., monitoring path 115, the instrumental operating parameters are selected. Guidelines for selecting operating parameters for ORS systems are provided in ASTM E 1865-97 Standard Guide for Open-Path Fourier Transform Infrared (OP/FT-IR) Monitoring of Gases and Vapors in Air and ASTM E 1982-98, Standard Practice for Open-Path Fourier Transform Infrared (OP/FT-IR) Monitoring of Gases and Vapors in Air.

Prior to monitoring for air contaminants of interest, a background spectrum is recorded. The background spectrum should not contain any spectral features of the low vapor pressure air contaminants of interest. Further, the background spectrum should not produce a baseline offset in the measured apparent absorbance spectrum. Thus, in some embodiments, the background spectrum is recorded along the same monitoring path, with the same instrumental configuration over which the air contaminants are to be monitored. A background spectrum can be selected from a plurality of spectra, e.g., a time series of spectra, acquired along the monitoring path during a monitoring period in which air contaminants are not present in the path. Guidelines for generating and selecting a background spectrum are provided in ASTM E 1865-97 Standard Guide for Open-Path Fourier Transform Infrared (OP/FT-IR) Monitoring of Gases and Vapors in Air and ASTM E 1982-98, Standard Practice for Open-Path Fourier Transform Infrared (OP/FT-IR) Monitoring of Gases and Vapors in Air.

Once a suitable background spectrum is generated, ORS spectra are recorded along the path at predetermined time intervals to provide a signal indicative of one of the path-integrated concentration and path-averaged concentration of the one or more target species, e.g., target species 145a and 145b, for example, as shown in FIG. 2A, comprising plume 145 along monitoring path 115. The ORS spectra are measured simultaneously with the one or more concentrations of the one or more target species at one or more predetermined locations, e.g., 115c, as determined by one or more point monitors 180.

The presently disclosed method further comprises correlating a temporal variation between one of the path-integrated concentration and path-averaged concentration and the one or more concentrations of the one or more target species at the one or more predetermined locations to estimate a maximum concentration of the one or more target species along the line of measurement. A representative algorithm for estimating the maximum concentration along a line of measurement is provided in Example 1. One of ordinary skill in the art would recognize that other algorithms also could be used to estimate the maximum concentration. Thus, the exemplary algorithm is provided in Example 1 to more completely describe an embodiment of the presently disclosed subject matter and not for the purposes of limitation.

Further, each air contaminant exhibits characteristic and unique features in an infrared (IR) spectrum, i.e., a "molecular fingerprint," which can be measured and exploited for identification purposes. The location and shape of these characteristic and unique features in the infrared spectrum depend on the identity of the air contaminant and the physical state, e.g., vapor phase, aerosol, adsorbed on particle, in which it exists.

The apparent absorbance spectrum of air contaminants also exhibits certain characteristics, which are indicative of the presence of a plume of the air contaminant in the optical beam. Representative air contaminants, including toxic chemicals listed as priority pollutants, compounds listed under the 1990 Clean Air Act Amendment, and noxious atmospheric gases are provided in Tables 1 and 2. Likewise, representative chemical warfare agents, the concentrations of which can be monitored by the presently disclosed subject matter are provided in Table 3.

TABLE 1

Estimated Minimum Detection Limits (MDLs) for Representative Air Contaminants[1]

| Compound | Class[2] | $v_{max}$ $(cm^{-1})$[3] | MDL (ppb-m)[3] | $v_{max}$ $(cm^{-1})$[4] | MDL (ppb-m)[4] |
|---|---|---|---|---|---|
| acetaldehyde | caa | 1761 | 2063 | 2729 | 6674 |
| acetonitrile | caa | 1463 | 8403 | 1042 | 46095 |
| acrolein | pp, caa | 1730 | 1297 | 958 | 4509 |
| acrylic acid | caa | 1726 | 639 | 1439 | 1326 |
| acrylonitrile | pp, caa | 954 | 3398 | 971 | 4548 |
| ammonia | pp | 967 | 620 | 931 | 718 |
| benzene | pp, caa | 673 | 266 | 3047 | 4449 |
| bis-2-chloroethyl)ether | pp, caa | 1138 | 2157 | 767 | 4372 |
| bromomethane | pp, caa | 1306 | 11547 | 2983 | 12455 |
| 1,3-butadiene | caa | 908 | 1445 | 1014 | 5719 |
| 2-butanone | pp, caa | 1745 | 1483 | 1175 | 3224 |
| carbon dioxide | ag | 2361 | 637 | 668 | 608 |
| carbon disulfide | pp, caa | 1541 | 191 | 1527 | 266 |
| carbon monoxide | cp | 2173 | 4583 | 2112 | 5417 |
| carbon tetrachloride | pp, caa | 795 | 178 | 773 | 1027 |
| carbon sulfide | caa | 2070 | 240 | 2051 | 330 |
| chlorobenzene | pp, caa | 740 | 1341 | 1483 | 3980 |
| chloroethane | pp, caa | 1288 | 6744 | 677 | 6871 |
| chloroform | pp, caa | 772 | 359 | 1219 | 1927 |
| chloromethane | pp, caa | 732 | 6652 | 1459 | 9517 |
| m-dichlorobenzene | pp | 1581 | 1266 | 784 | 1305 |
| o-dichlorobenzene | pp | 749 | 1428 | 1462 | 5142 |
| dichlorodifluoromethane | pp | 1161 | 294 | 921 | 303 |
| 1,1-dichloroethane | pp, caa | 705 | 2049 | 1060 | 3053 |
| 1,2-dichloroethane | pp, caa | 731 | 1983 | 1237 | 6803 |
| 1,1-dichloroethene | pp | 869 | 1241 | 793 | 1814 |
| 1,2-dichloroethene | pp, caa | 864 | 5024 | | |
| dichloromethane | pp, caa | 750 | 1174 | 1276 | 4113 |
| 1,1-dimethylhydrazine | caa | 2775 | 1962 | 909 | 3774 |
| ethylbenzene | pp, caa | 2975 | 2031 | 697 | 2277 |
| ethylene oxide | pp, caa | 3066 | 987 | 872 | 3327 |
| formaldehyde | caa | 1745 | 1248 | 2802 | 2581 |
| hexane | caa | 2964 | 1023 | 1467 | 7710 |
| hydrogen chloride | caa | 2945 | 3164 | 2822 | 3620 |
| hydrogen fluoride | caa | 4038 | 578 | 3877 | 761 |
| hydrogen sulfide | caa | 1293 | 535003 | | |
| isooctane | caa | 2961 | 554 | | |
| methane | ag | 3017 | 1597 | 1305 | 2998 |
| methanol | caa | 1033 | 1249 | 2982 | 5933 |
| methylmethacrylate | caa | 1169 | 1199 | 1748 | 1341 |
| nitric oxide | ag | 1894 | 4388 | 1843 | 6816 |
| nitrobenzene | pp, caa | 1553 | 852 | 1355 | 1049 |
| nitrogen dioxide | cp, ag | 1629 | 540 | 1599 | 742 |
| nitrous oxide | ag | 2213 | 932 | 1300 | 3946 |
| ozone | cp | 1054 | 2533 | 1040 | 3971 |
| phosgene | caa | 849 | 318 | 1832 | 667 |
| phosphine | caa | 2326 | 7699 | 992 | 12468 |
| propionaldehyde | caa | 1762 | 2305 | 2992 | 4107 |
| propylene oxide | caa | 3001 | 2838 | 837 | 4549 |
| styrene | caa | 695 | 1720 | 909 | 2908 |
| sulfur dioxide | cp | 1377 | 372 | | |
| sulfur hexafluoride | tracer | 947 | 42 | 615 | 420 |
| tetrachloroethene | pp, caa | 915 | 708 | 781 | 2654 |
| toluene | pp, caa | 728 | 1632 | 3018 | 3583 |
| 1,1,1-trichloroethene | pp, caa | 725 | 533 | 1088 | 1183 |
| 1,1,2-trichloroethane | pp, caa | 742 | 1615 | 941 | 7933 |
| trichloroethene | pp, caa | 849 | 1173 | 944 | 1578 |
| trichlorofluoromethane | pp | 846 | 178 | 1084 | 634 |
| vinyl acetate | caa | 1225 | 688 | 1790 | 1327 |

TABLE 1-continued

Estimated Minimum Detection Limits (MDLs)
for Representative Air Contaminants[1]

| Compound | Class[2] | $v_{max}$ (cm$^{-1}$)[3] | MDL (ppb-m)[3] | $v_{max}$ (cm$^{-1}$)[4] | MDL (ppb-m)[4] |
|---|---|---|---|---|---|
| vinyl chloride | pp, caa | 942 | 2824 | 1620 | 3643 |
| vinylidene chloride | caa | 868 | 1669 | 1086 | 2501 |
| m-xylene | pp, caa | 768 | 1601 | 690 | 3825 |
| o-xylene | pp, caa | 741 | 1070 | 2949 | 5797 |
| p-xylene | pp, caa | 795 | 1765 | 2936 | 3340 |

[1]The minimum detection limits (MDLs) in units of the concentration-pathlength product $(bC)_{min}$ were estimated by using the following equation, $(bC)_{min} = A_{min}/a$ wherein: $A_{min}$ is the minimum detectable absorbance, for example, three times the root-mean-square baseline noise; a is the absorptivity, which can be calculated from the following equation: $a = A/bC$ wherein: A is the absorbance at a specified wavenumber; b is the pathlength at which the spectrum was measured; and C is the concentration; with values of the absorptivity calculated from 1-cm$^{-1}$ reference spectra with triangular apodization from a commercially-available spectral library (Infrared Spectra for Quantitative Analysis of Gases, Infrared Analysis, Inc., Anaheim, California, United States of America) and a minimum detectable absorbance of $1 \times 10^{-3}$.
[2]Classification: priority pollutant (pp); criteria pollutant (cp); hazardous air pollutant from the 1990 Clean Air Act Amendment (caa); and atmospheric gas (ag).
[3]Peak position and MDL for the strongest absorption band in a first spectral region.
[4]Peak position and MDL for the second strongest absorption band in a second spectral region.

TABLE 2

Air Contaminants That Can Be Monitored
by a Tunable Diode Laser ORS System.

| Compound | Estimated MDLs (ppb-m) |
|---|---|
| hydrogen fluoride (HF) | 10 |
| hydrogen chloride (HCl) | 25 |
| hydrogen bromide (HBr) | 100 |
| hydrogen iodide (HI) | 250 |
| hydrogen cyanide (HCN) | 100 |
| carbon monoxide (CO) | 5000 |
| carbon dioxide ($CO_2$) | 250 |
| methane ($CH_4$) | 250 |
| acetylene ($C_2H_2$) | 750 |
| ethylene ($C_2H_4$) | 2500 |
| ethane ($C_2H_6$) | 2500 |
| propane ($C_3H_8$) | |
| vinyl chloride ($CH_2CHCl$) | 250 |
| nitric oxide (NO) | 7500 |
| nitrogen dioxide ($NO_2$) | 2500 |
| ammonia ($NH_3$) | 2000 |
| hydrogen sulfide ($H_2S$) | 5000 |

The estimated detection limits of OP-IR methods for detecting representative chemical warfare agents (CWAs) in the vapor phase are compared to point source monitoring methods in Table 3. As shown in Table 3, OP-IR methods are capable of detecting representative CWAs in the vapor phase at levels well below the Immediately Dangerous to Life and Health (IDLH) and Acute Exposure Guideline Level (AEGL) limits for these CWAs.

The wide range of values shown in Table 3 depends on many measurement variables, such as source temperature, source modulation, type of detector, type of infrared source, pathlength through the plume relative to the optical path length, atmospheric conditions, and the like. Yet, for each specific measurement-and-system condition, the detection limit can be accurately determined, thereby screening out unwanted false positive readings. This feature allows the users to exploit the benefits of path-integrated measurements, i.e., better capture of the entire plume, and still make use of several complementary sensitive point monitors for detection confirmation. These point monitors by themselves (without path-integrated data) can bias—most typically by underestimation of the extent of the plume—or worse, miss the entire

TABLE 3

Estimated Monitoring Ranges for Representative
Chemical Agents in the Vapor Phase

| Chemical Agent | Active OP-IR (µg/m$^3$) | Passive OP-IR (µg/m$^3$) | NRT (µg/m$^3$) | DAAMS (µg/m$^3$) | IDLH (µg/m$^3$) | AEGL (µg/m$^3$) |
|---|---|---|---|---|---|---|
| GB | $1 \times 10^{-4}$ to 1 | 10 to 80 | $2.5 \times 10^{-5}$ to $4.5 \times 10^{-3}$ | $5 \times 10^{-7}$ to $5 \times 10^{-4}$ | $5 \times 10^{-2}$ | $5 \times 10^{-2}$ |
| VX | $1 \times 10^{-4}$ to 1 | 10 to 80 | $2.5 \times 10^{-6}$ to $5 \times 10^{-3}$ | $5 \times 10^{-7}$ to $5 \times 10^{-5}$ | $8 \times 10^{-3}$ | $6 \times 10^{-3}$ |
| HD | $1 \times 10^{-4}$ to 1 | 10 to 80 | $1 \times 10^{-4}$ to $2 \times 10^{-2}$ | $2 \times 10^{-5}$ to $7 \times 10^{-4}$ | na | $1 \times 10^{-1}$ |

NRT = near real-time; DAAMS = depot area air monitoring system; IDLH = Immediately Dangerous to Life and Health; AEGL = Acute Exposure Guideline Level na = not available plume. When multiple beams are scanned in different directions and path-lengths, a radial plume mapping (RPM) method can be applied to retrieve spatial gradients and profiles across the plume. Such systems can detect more than 100 air contaminants, such as but not limited to, TICs and/or CWAs, simultaneously.

One of ordinary skill in the art would recognize that any air contaminant and/or chemical warfare agent and/or particulate matter that exhibits absorption bands or spectral features, such as a baseline offset, in the mid-infrared or near-infrared spectral region can be monitored by the presently disclosed methods, systems, and computer program products.

II.C. Computer Program Product for Correlating Temporal Variations Between Simultaneous Measurements of at Least One Point Monitor and a Monitor Capable of Measuring a Path-integrated or Path-Averaged Concentration In some embodiments, the presently disclosed subject matter comprises computer-executable instructions embodied in a computer-readable medium, wherein the computer-executable instructions produce a computer program product for correlating temporal variations between simultaneous measurements of at least one point monitor and monitor capable of measuring one of a path-integrated concentration and a path-averaged concentration, including, but not limited to an optical remote sensing (ORS) monitor.

Figure 4:
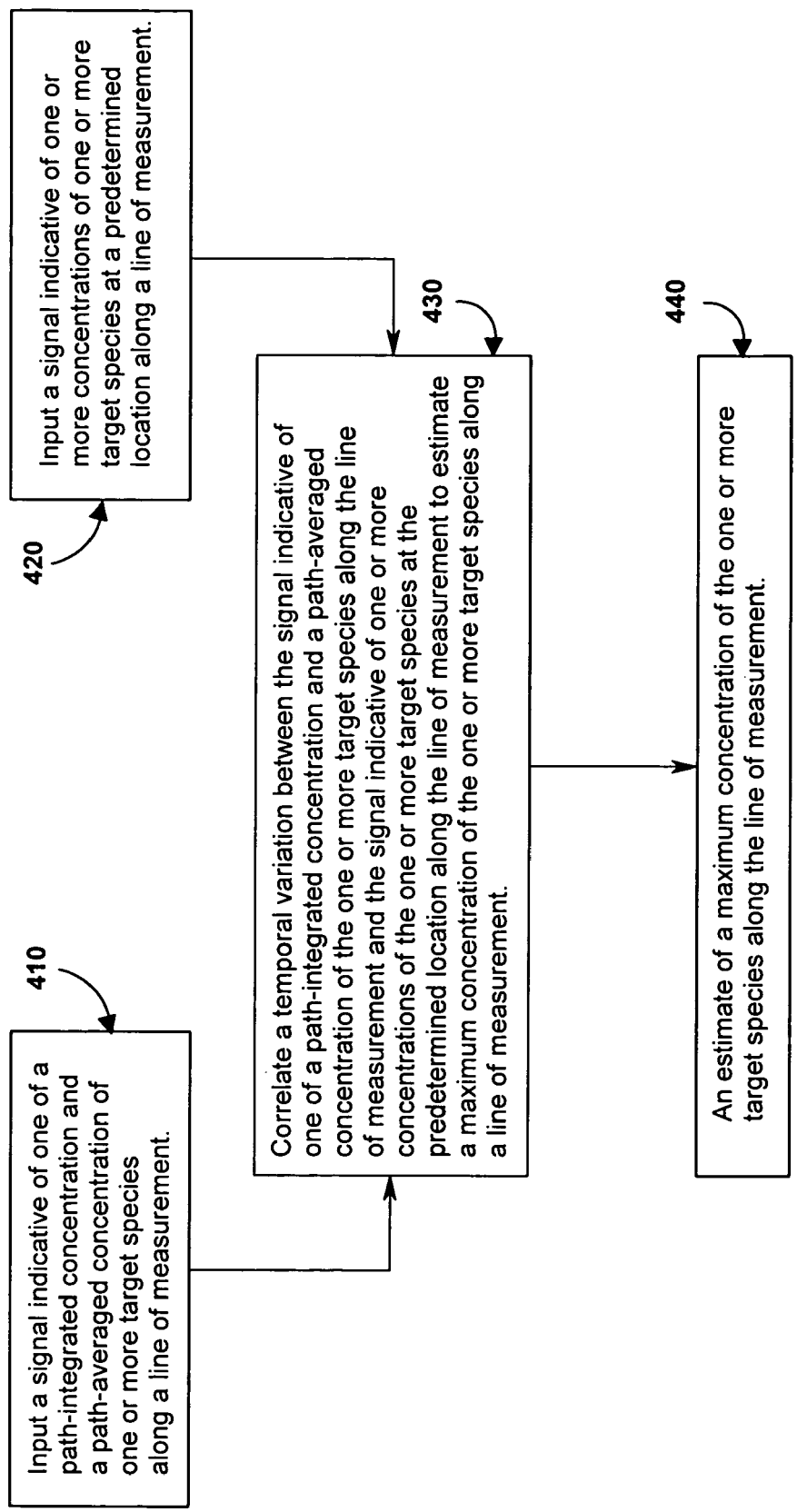
FIG. 4 is a flow chart showing an embodiment of the presently disclosed computer-executable instructions for estimating a maximum concentration of one or more target species along a line of measurement.

Referring now to FIG. 4, in some embodiments, the presently disclosed computer-executable instructions comprise step 410. In some embodiments, step 410 comprises inputting a signal indicative of one of a path-integrated concentration and a path-averaged concentration of one or more target species along a line of measurement. The signal indicative of one of a path-integrated concentration and a path-averaged concentration can be produced, for example, by ORS monitor 20, as provided in FIGS. 2A, 2B, 2C, 3A, and 3B, wherein a signal indicative of an apparent absorbance spectrum of gases, vapors, aerosol, particles, and combinations thereof (e.g., target species 145$a$ and 145$b$ shown, for example, in FIG. 2A) comprising plume 145 along monitoring path 115 is produced by detector 110, in some embodiments, transmitted to processor 150, and further, in some embodiments, stored in memory 155. In some embodiments, processor 150 is operationally coupled to processor 200. Thus, in some embodiments, step 410 comprises inputting the signal transmitted to processor 150 and/or stored in memory 155, to processor 200.

Referring once again to FIG. 4, in some embodiments, the presently disclosed computer-executable instructions comprise step 420. In some embodiments, step 420 comprises inputting a signal indicative of one or more concentrations of one or more target species at one or more predetermined locations along a line of measurement. Referring now to FIGS. 1A, 1B, 1C, 2A, and 2B, in some embodiments, the signal indicative of one or more concentrations of one or more target species, e.g., target species 145$a$ and 145$b$, comprising plume 145 at predetermined location 115$c$ along a measurement, e.g., monitoring path 115, is produced by point monitor 180, and in some embodiments, transmitted to processor 190, and further, in some embodiments, stored in memory 155. In some embodiments, processor 190 is operationally coupled to processor 200. Thus, in some embodiments, step 420 comprising inputting the signal transmitted to processor 190 and/or stored in memory 195 to processor 200.

Referring once again to FIG. 4, in some embodiments, the presently disclosed computer-executable instructions comprise step 430. In some embodiments, step 430 comprises correlating a temporal variation between the signal indicative of one of a path-integrated concentration and a path-averaged concentration of the one or more target species, e.g., target species 145$a$ and 145$b$, along the line of measurement, e.g., the input signal from step 410, and the signal indicative of one or more concentrations of the one or more target species at the one or more predetermined locations along the line of measurement, e.g., the input signal from step 420, to estimate a maximum concentration of the one or more target species along the line of measurement.

Referring once again to FIG. 4, step 430, i.e., correlating a temporal variation between the signal indicative of one of a path-integrated concentration and a path-averaged concentration of the one or more target species along the line of measurement, e.g., the input signal from step 410, and the signal indicative of one or more concentrations of the one or more target species at the one or more predetermined locations along the line of measurement, e.g., the input signal from step 420, produces computer-program product 440, an estimate of a maximum concentration of the one or more target species along the line of measurement.

A representative algorithm for estimating the maximum concentration along a line of measurement is provided in Example 1. One of ordinary skill in the art would recognize that other algorithms also could be used to estimate the maximum concentration. Thus, the exemplary algorithm is provided in Example 1 to more completely describe an embodiment of the presently disclosed subject matter and not for the purposes of limitation.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

The temporal variability in concentrations as measured by a point monitor as compared to the temporal variability of a path-integrated or path-averaged concentration measured, for example, by an ORS monitor, can be used to calculate the temporal coefficient of variation, CVT. The temporal coefficient of variation, CVT, can be calculated as shown in equation (1):

$$CV_T = \frac{1}{\langle C_{beam} \rangle} \sqrt{\sum_n (C_{point} - C_{beam})^2} \qquad (1)$$

wherein:

n is the number of sequential and synchronized data points for the point monitor and ORS measurements; and $C_{point}$ and $C_{beam}$ are the concentrations of the one or more target species at the point monitor and at the beam, respectively.

Figure 5:
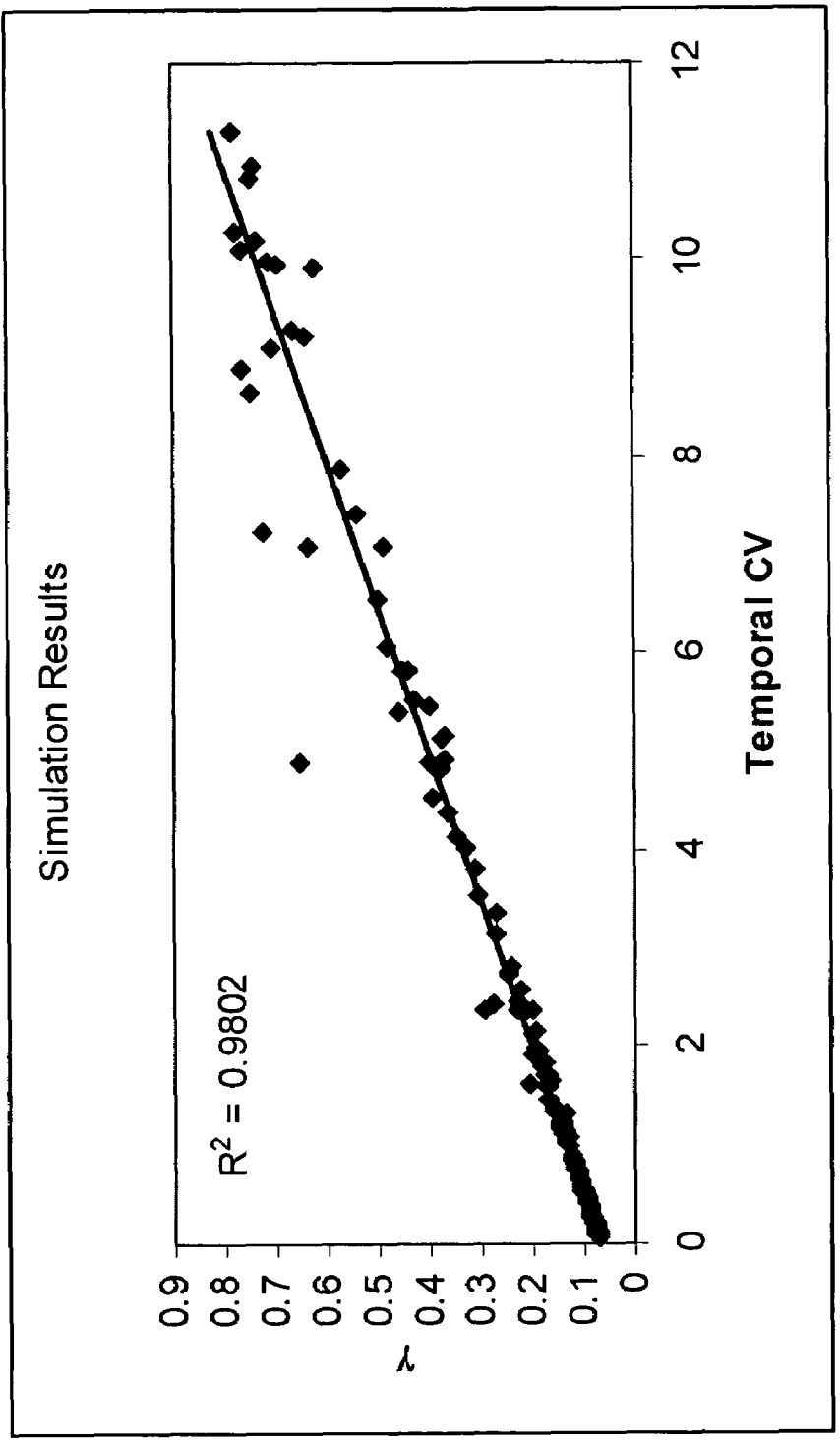
FIG. 5 is a scatterplot of computer simulation results showing the relationship of the variable gamma (y) to CVT, the temporal coefficient of variation.

The temporal coefficient of variation, $CV_T$, can be used to estimate the variable gamma ($\gamma$). Referring now to FIG. 5, simulation data show a linear relationship between $\gamma$ and $CV_T$. The variable $\gamma$ can then be used to calculate the maximum concentration according to equation (2):

$$C_{max} = \gamma \cdot n(C_{beam}) \qquad (2)$$

Referring once again to FIG. 5, 400 random plume events crossing the fenceline were introduced in the simulation. For each event, the computer selected an underlying plume width and peak location. Fifteen consecutive measurement episodes (n=15) on the synchronized and simulated point and ORS monitors constituted one plume event traversed through the fenceline. The peak concentration, the beam concentration (the area under the concentration profile divided by the pathlength) and the $CV_T$ were calculated for all plume events and were plotted against each other. FIG. 5 demonstrates the linear relationship between the plume width (as expressed by the ratio between the peak concentration, $C_{max}$, and beam concentration, $C_{beam}$, i.e., the variable gamma ($\gamma$) of equation 2, and the temporal coefficient of variation. In practice, this linear relationship can allow the estimate of the plume width and maximum concentration by calculating $CV_T$.

Example 2

Figure 6:
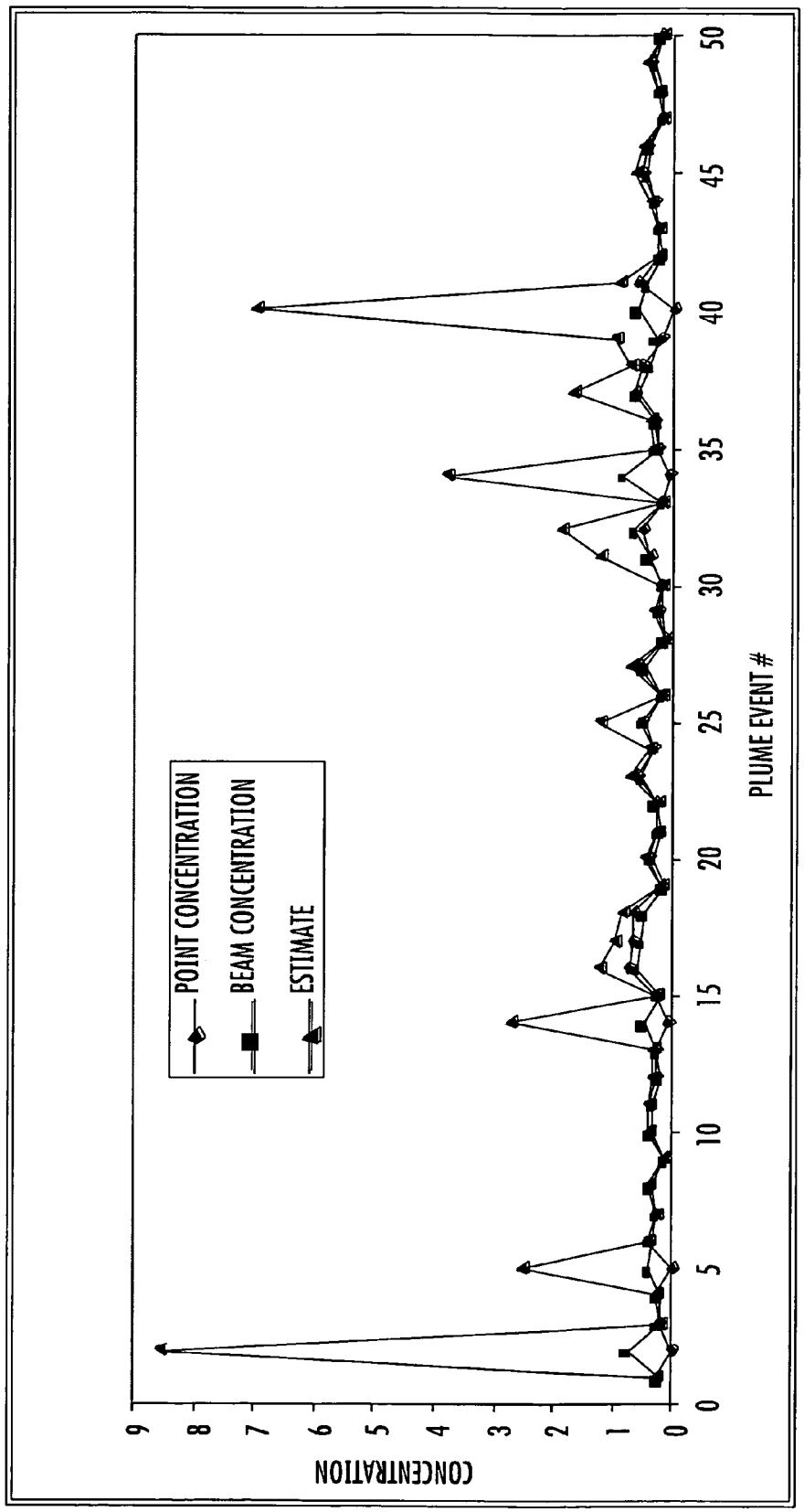
FIG. 6 is a simulated plot of peak concentrations of a target species crossing a fenceline estimated by an embodiment of the presently disclosed method.

Referring now to FIG. 6, the results from 50 plume events in the computational simulation are shown. The estimates of the maximum concentration provided by the presently disclosed method, in some embodiments, provide upper bound concentrations crossing the fenceline. The extreme estimates reflect simulations wherein the point monitor missed the plume and the beam concentration is relatively high.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for estimating a maximum concentration of one or more target species along a line of measurement, the method comprising:
    (a) providing a first monitor capable of producing a signal indicative of one of a path-integrated concentration and a path-averaged concentration of the one or more target species along a line of measurement;
    (b) selecting a line of measurement comprising a first end point and a second end point;
    (c) positioning the first monitor along the line of measurement at a monitoring path defined by the first end point and the second end point of the line of measurement;
    (d) positioning at least one point monitor at one or more predetermined locations between the first end point and the second end point of the line of measurement, wherein the at least one point monitor is capable of producing a signal indicative of one or more concentrations of the one or more target species at the one or more predetermined locations;
    (e) simultaneously measuring one of the path-integrated concentration and path-averaged concentration and the one or more concentrations of the one or more target species at the one or more predetermined locations; and
    (f) correlating a temporal variation between one of the path-integrated concentration and path-averaged concentration and the one or more concentrations of the one or more target species at the one or more predetermined locations to estimate a maximum concentration of the one or more target species along the line of measurement.

2. The method of claim 1, wherein the one or more target species comprises an air contaminant.

3. The method of claim 2, wherein the air contaminant is selected from the group consisting of a toxic industrial chemical, a chemical warfare agent, and particulate matter.

4. The method of claim 1, wherein the line of measurement comprises a monitoring path along the perimeter of a facility.

5. The method of claim 4, wherein the facility is a facility having one or more air contaminants disposed therein.

6. The method of claim 1, wherein the first monitor is selected from the group consisting of an open-path Fourier transform infrared (OP-FTIR) monitor and a tunable diode laser (TDL) monitor.

7. The method of claim 1, wherein the predetermined location of the at least one point monitor is about a midpoint between the first end point and the second end point of the line of measurement.

8. The method of claim 1, comprising one point monitor.

9. A system for estimating a maximum concentration of one or more target species along a line of measurement, the system comprising:
    (a) a first monitor capable of producing a signal indicative of one of a path-integrated concentration and a path-averaged concentration of the one or more target species along a line of measurement, wherein said first monitor comprises at least one detector;
    (b) at least one point monitor adapted for positioning at one or more predetermined locations between the first end point and the second end point of the line of measurement, wherein the at least one point monitor is capable of producing a signal indicative of one or more concentrations of the one or more target species at the one or more predetermined locations;
    (c) a memory in which a plurality of machine instructions are stored; and
    (d) at least one processor that is coupled to the at least one detector, the at least one point monitor, and the memory, wherein the processor is capable of executing the plurality of machine instructions stored in the memory, causing the processor to:
        (i) simultaneously record the signal indicative of one of a path-integratedconcentration and a path-averaged concentration of the one or more target species along the line of measurement and the signal indicative of one or more concentrations of the one or more target species at the one or more predetermined locations; and
        (ii) correlate a temporal variation between the signal indicative of one of a path-integrated concentration and a path-averagedconcentration of the one or more target species along the line of measurement and the signal indicative of one or more concentrations of the one or more target species at the one or more predetermined locations to estimate a maximum concentration of the one or more target species along the line of measurement.

10. The system of claim 9, wherein the first monitor is selected from the group consisting of an open-path Fourier transform infrared (OP-FTIR) monitor and a tunable diode laser (TDL) monitor.

11. The system of claim 9, comprising one point monitor.

12. A computer program product comprising computer-executable instructions embodied in a computer-readable medium for performing steps comprising:
    (a) inputting a signal indicative of one of a path-integrated concentration and a path-averaged concentration of one or more target species along a line of measurement; (
    b) inputting a signal indicative of one or more concentrations of one or more target species at one or more predetermined locations along a line of measurement; and
    (c) correlating a temporal variation between the signal indicative of one of a path-integrated concentration and a path-averaged concentration of the one or more target species along the line of measurement and the signal indicative of one or more concentrations of the one or more target species at the one or more predetermined locations along the line of measurement to estimate a maximum concentration of the one or more target species along the line of measurement.

* * * * *